United States Patent
Brabander et al.

(10) Patent No.: US 7,429,616 B2
(45) Date of Patent: Sep. 30, 2008

(54) SYNTHESIS AND COMPLETE STEREOCHEMICAL ASSIGNMENT OF PSYMBERIN/IRCINIASTATIN FOR USE AS ANTITUMOR COMPOUNDS

(75) Inventors: Jef De Brabander, Lewisville, TX (US); Xin Jiang, Dallas, TX (US)

(73) Assignee: Board of Regents, University of Texas System, Austin, TX (US)

( * ) Notice: Subject to any disclaimer, the term of this patent is extended or adjusted under 35 U.S.C. 154(b) by 250 days.

(21) Appl. No.: 11/182,069

(22) Filed: Jul. 15, 2005

(65) Prior Publication Data
US 2007/0015821 A1  Jan. 18, 2007

(51) Int. Cl.
*A61K 31/35* (2006.01)
*C07D 311/02* (2006.01)

(52) U.S. Cl. .................. 514/457; 549/283
(58) Field of Classification Search ............ 549/283; 514/457
See application file for complete search history.

(56) References Cited

FOREIGN PATENT DOCUMENTS

| EP | 0 039 051 B1 | 7/1985 |
|---|---|---|
| WO | WO 2005/054809 A2 | 6/2005 |

OTHER PUBLICATIONS

George R. Pettit et al., "Antineoplastic Agents. 520. Isolation and Structure of Irciniastatins A and B from the Indo-Pacific Marine Sponge *Ircinia ramosa*[1]" J. Med. Chem. 2004, 47, 1149-1152.
Robert H. Cichewicz et al., "Psymberin, A Potent Sponge-Derived Cytotoxin from *Psammocinia* Distantly Related to the Pederin Family", Organic Letters, 2004, vol. 6, No. 12, 1951-1954.
Stephen M. Berge et al., "Pharmaceutical Salts", Journal of Pharmaceutical Science, vol. 66, No. 1, Jan. 1977, pp. 1-19.
Leif A. Svensson et al., "The Design and Bioactivation of Presystemically Stable Prodrugs", Drug Metabolism Reviews, 19(2), pp. 165-194 (1988).
Prabhakar X. Jadhav et al., "Chiral Synthesis via Organoboranes. 5. Asymmetric Allylboration via Chiral Allyldialkylboranes. Synthesis of Homoallylic Alcohols with Exceptionally High Enantiomeric Excess", J. Org. Chem. 1986, 51, 432-439.
David A. Evans et al., "Diastereoselective Aldol Reactions of β-Silyloxy Ethyl Ketones. Application to the Total Synthesis of Bafilomycin $A_1$", Tetrahedron Letters, vol. 34, No. 43, pp. 6871-6874, 1993.

(Continued)

*Primary Examiner*—Janet L. Andres
*Assistant Examiner*—Raymond Covington
(74) *Attorney, Agent, or Firm*—Foley & Lardner LLP

(57) ABSTRACT

The invention relates to the synthesis and complete stereochemical assignments of cytotoxic compounds such as compound 28-a and its stereoisomers:

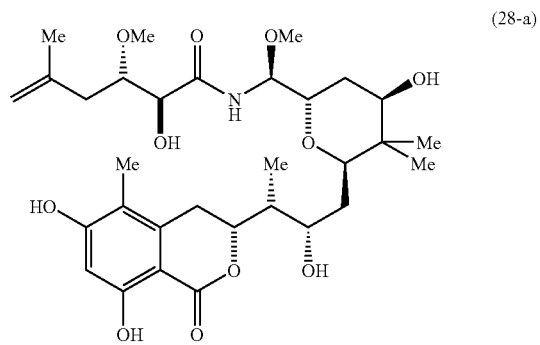

The invention further provides processes for making the compounds, their synthetic intermediates, and for methods of using the compounds and their pharmaceutical compositions for the treatment of neoplastic diseases.

20 Claims, 7 Drawing Sheets

OTHER PUBLICATIONS

J.P. Lambooy, "The Synthesis of the 2,4-Dihydroxymethylphenylalanines and the Possible Sites of the Linkages between Tyrosinase and Substrate[1]", Contribution from the Department of Physiology, the University of Rochester School of Medicine and Dentistry, vol. 78, Feb. 20, 1956, pp. 771-774.

Sukanta Kamila et al., "Application of directed metallation in synthesis. Part 3: Studies in the synthesis of (±)- semivioxanthin and its analogues", Tetrahedron 59 (2003), pp. 1339-1348.

Ramon Casas et al., "Ortho-metalated Aromatic Tertiary Amides: New Synthetic Applications", Tetrahedron Letters, vol. 36, No. 7, 1995, pp. 1039-1042.

Gary E. Keck et al., "A Direct and Mild Conversion of Tertiary Aryl Amides to Methyl Esters Using Trimethyloxonium Tetrafluoroborate: A Very Useful Complement to Directed Metalation Reactions", Tetrahedron 56 (2000), 9875-9883.

Paul R. Johnson et al., "Condensation of Crotonic and Tiglic Acid Dianions with Aldehydes and Ketones", J. Org. Chem. 1984, 49, 4424-4429.

Katsumi Kubota et al., "A Highly Practical and Enantioselective Reagent for the Allylation of Aldehydes", Angew. Chem. Int. Ed. 2003, 42, No. 8, pp. 946-948.

Hideya Takahashi et al., "A Catalytic Enantioselective Reaction using a $C_2$-Symmetric Disulfonamide as a Chiral Ligand: Alkylation of Aldehydes Catalyzed by Disulfonamide-Ti(O-i-Pr)$_4$-Dialkyl Zinc System", Tetrahedron vol. 48, No. 27, pp. 5691-5700,1992.

David A. Evans et al., "Reduction of β-Hydroxy Ketones with Catecholborane. A Stereoselective Approach to the Synthesis of Syn 1,3-Diols", J. Org. Chem. 1990, 55, 5190-5192.

Talit Ghaffar et al., "A New Homogeneous Platinum Containing Catalyst for the Hydrolysis of Nitriles", Tetrahedron Letters, vol. 36, No. 47, pp. 8657-8660, 1995.

Talit Ghaffar et al., "The catalytic hydration of nitriles to amides using a homogeneous platinum phosphinito catalyst", Journal of Molecular Catalysis A: Chemical 160 (2000) 249-261.

W. Clark Still et al., "Rapid Chromatographic Technique for Preparative Separations with Moderate Resolution", J. Org. Chem. vol. 43, No. 14, 1978, 2923-2925.

Thomas Trieselmann et al., "Conformational Analysis of *oligo*-1,3-Dioxanylmethanes", Eur. J. Org. Chem., 2002, 1292-1304.

Scott. D. Rychnovsky et al., "Analysis of Two $^{13}$C NMR Correlations for Determining the Stereochemistry of 1,3-Diol Acetonides", J. Org. Chem. 1993, 58, 3511-3515.

Zbyszek Otwinowski et al., "Processing of X-Ray Diffraction Data Collected in Oscillation Mode", Methods in Enzymology, vol. 276, 1997, pp. 307-327.

Xin Jiang et al., "Synthesis and Complete Stereochemical Assignment of Psymberin/Irciniastatin A", J. Am. Chem. Soc. 2005, 127, pp. 11254-11255.

SYNTHESIS AND COMPLETE STEREOCHEMICAL ASSIGNMENT OF PSYMBERIN/IRCINIASTATIN FOR USE AS ANTITUMOR COMPOUNDS

STATEMENT OF GOVERNMENTAL INTEREST

The subject matter of this application was supported in part by research Grant No. CA090349 from the National Institutes for Health (NIH), Bethesda, Md., and the U.S. Government may therefore have certain rights in the invention.

BACKGROUND OF THE INVENTION

The present invention relates generally to the field of organic synthesis and stereochemical assignments of compounds exhibiting efficacy against neoplastic diseases.

Natural products that elicit a specific and unique biological response in mammalian cells represent valuable tools for new pharmaceuticals for the treatment for various disease states. In this context the recent isolation of irciniastatin and psymberin from the marine sponges *Ircinia ramose* and *Psammocinia* sp respectively is noteworthy. Both irciniastatins and psymberin have potent inhibitory activity in human tumor cell assays. They also have partial structural resemblance to the pederin family of natural products and therefore could share the latter's well-documented pharmacological role as potent eukaryotic protein synthesis inhibitors. The total synthesis of these natural products, analogs thereof, and probe-reagents for mode-of-action studies should provide a solid foundation for lead identification and preclinical studies in the area of human cancer.

In 2004, two research groups led by Pettit and Crews independently disclosed the isolation of structurally novel, constitutionally identical cytotoxins. Both irciniastatin and psymberin (shown below) were isolated based on their potent inhibitory activity in human tumor cell assays. Irciniastatin A was isolated from the Indo-Pacific marine sponge *Ircinia ramose* (Pettit, G. R. et al. *J. Med. Chem.* 2004, 47, 1149), whereas psymberin was obtained from a marine sponge *Psammocinia* sp. collected from the waters of Papua New Guinea (Cichewicz, R. H. et al. *Org. Lett.* 2004, 6, 1951). See also WO 2005/054809.

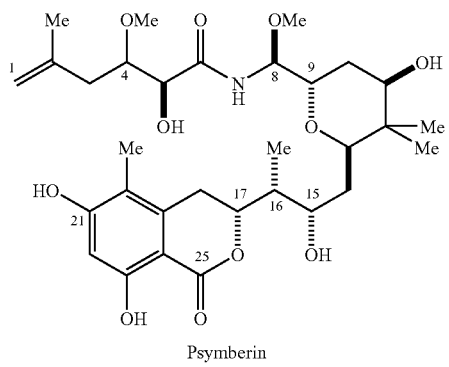

Psymberin

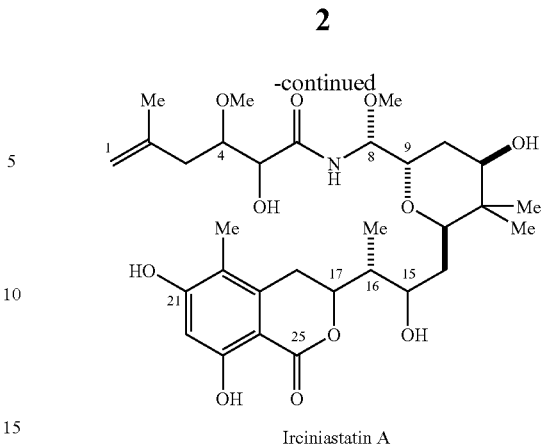

Irciniastatin A

High field multidimensional NMR studies and chiroptical data (Circular Dichroism; Cotton effect at n→Π* transition of dihydroisocoumarin) substantiated the proposed relative and absolute configuration for psymberin, except for the undefined configuration at $C_4$ (Cichewicz, R. H. et al., supra). The relative stereochemistry of irciniastatin A was only resolved for the $C_8$-$C_{13}$ aminal fragment (Pettit, G. R. et al., supra). Notably, the $C_8$-aminal configuration in irciniastatin A (based on nOe-data) was opposite to the corresponding center assigned for psymberin. No copies of actual NMR spectra were included in the irciniastatin publication (Pettit, G. R. et al., supra) and, combined with the fact that spectra for irciniastatin and psymberin were acquired in different NMR solvents, no conclusion could be drawn whether these two constitutionally ident ical metabolites bear an identical or diastereomeric correspondence. Therefore, a need exists to define the stereochemistry of these purified active cytotoxins, together with synthetic routes to make them.

SUMMARY OF THE INVENTION

This invention satisfies this need and others by providing, in one embodiment, a pharmaceutically acceptable salt or prodrug of the compound of formula 28-a:

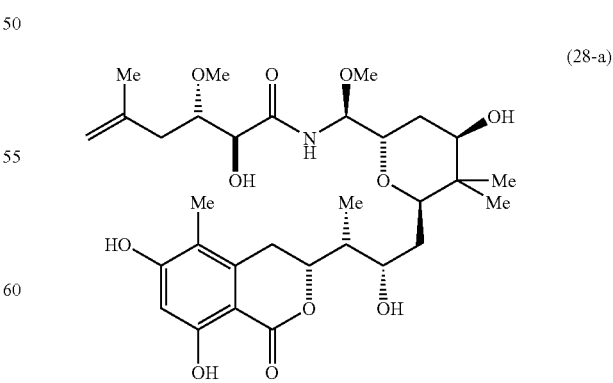

(28-a)

In another embodiment, the invention provides a compound having one of the following formulae:

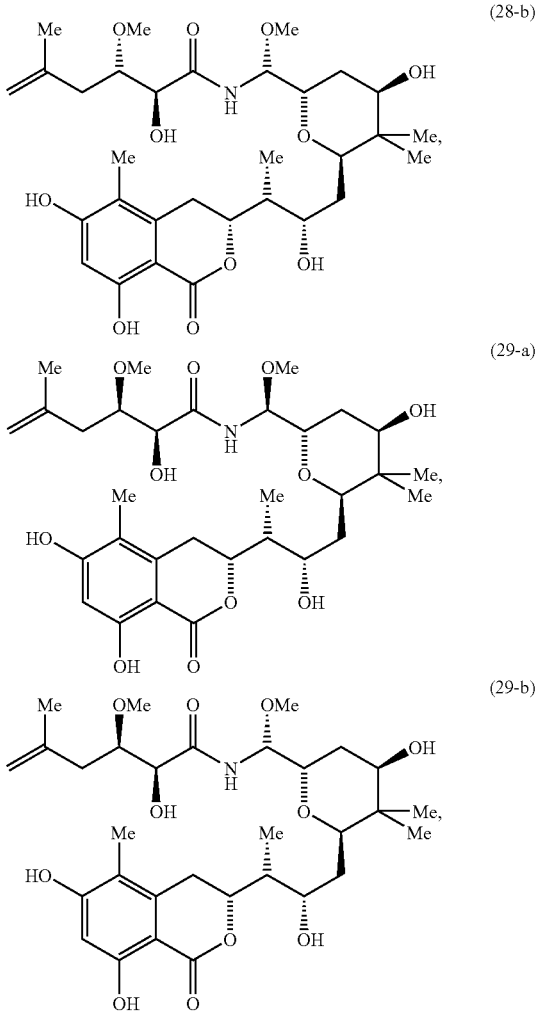

or a pharmaceutically acceptable salt, solvate, or prodrug thereof. Other embodiments contemplate pharmaceutical compositions comprising a compound of the invention and a pharmaceutically acceptable carrier.

Still another embodiment of the invention is a method for treating a subject suffering from a neoplastic disease. The method comprises administering to the subject a therapeutically effective amount of a compound according to formula 28-a, 28-b, 29-a, or 29-b.

The invention also provides, in other embodiments, processes for preparing the compound of formula 28-a and certain synthetic intermediate compounds. In that regard, other embodiments relate to those synthetic intermediate compounds.

DETAILED DESCRIPTION

Figure 1:
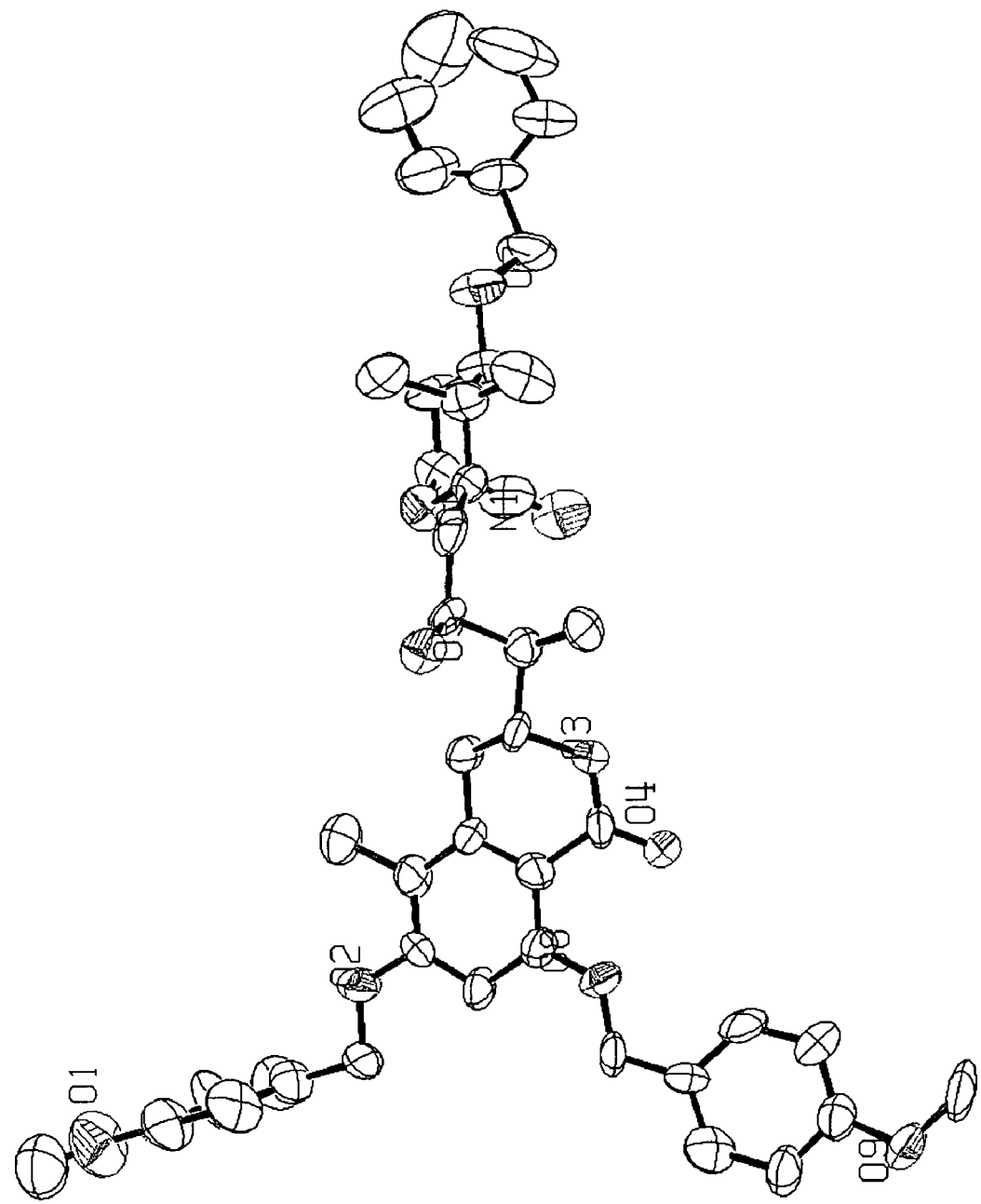
FIG. 1 is an ORTEP of compound 22a (hydrogen atoms are not shown for the sake of clarity).

The inventors discovered highly convergent syntheses of the cytotoxic compounds according to the invention. Spectrochemical analyses of the compounds led, for the first time, to correct stereochemical assignments for all chiral centers. Those compounds, pharmaceutically acceptable salts, and prodrugs thereof are useful for treating neoplastic diseases in a subject.

Compounds

As noted above, the invention provides for compounds of formulae 28-a, 28-b, 29-a, and 29-b. These compounds can also exist as pharmaceutically acceptable salts, solvates, or prodrugs as more fully described below.

In general, a "salt" refers to a salt form of a free base compound of the present invention, as appreciated by persons of ordinary skill in the art. Salts can be prepared by conventional means known to those who are skilled in the art. The term "pharmaceutically-acceptable", when used in reference to a salt, refers to salt forms of a given compound, which are within governmental regulatory safety guidelines for ingestion and/or administration to a subject. The term "pharmaceutically-acceptable salts" embraces salts commonly used to form alkali metal salts and to form addition salts of free acids or free bases. The nature of the salt is not critical, provided that it is pharmaceutically-acceptable.

The category of suitable pharmaceutically-acceptable base addition salts of compounds of formulae 28-a, 28-b, 29-a, and 29-b encompasses metallic salts, such as salts made from aluminum, calcium, lithium, magnesium, potassium, sodium and zinc, as well as salts made from organic bases, including primary, secondary and tertiary amines, and substituted amines including cyclic amines, such as caffeine, arginine, diethylamine, N-ethyl piperidine, aistidine, glucamine, isopropylamine, lysine, morpholine, N-ethyl morpholine, piperazine, piperidine, triethylamine, and trimethylamine. In one embodiment, the pharmaceutically acceptable salt is the lithium, sodium, or potassium salt.

Additional examples of such acid and base addition salts can be found in Berge et al., *J. Pharm. Sci.* 66: 1 (1977). All of these salts can be prepared by conventional means from the corresponding compound of the invention by reacting, for example, the appropriate acid or base with the compound of formula 28-a, 28-b, 29-a, and 29-b, respectively.

The present invention also contemplates prodrugs of the compounds described here. A "prodrug" is a compound that, when administered to the body of a subject, such as a mammal, undergoes a conversion in situ that yields an active agent of formula 28-a, 28-b, 29-a, or 29-b. More specifically, a prodrug is an active or inactive, "masked" compound that is modified chemically through in vivo physiological action, such as hydrolysis, metabolism and the like, into a compound of this invention following administration of the prodrug to a subject or patient. The suitability and techniques of making and using prodrugs are well known. In one embodiment, for example, the invention provides for an ester prodrug. A discussion of prodrugs involving esters appears in Svensson and Tunek, *Drug Metabolism Reviews* 165 (1988), and in Bundgaard, DESIGN OF PRODRUGS (Elsevier 1985).

Also, hydroxy groups can be masked as esters and ethers, respectively. EP 039,051 (Sloan and Little, Apr. 11, 1981) discloses Mannich-base hydroxamic acid prodrugs, along with their preparation and use. Thus, one or more hydroxy substituents in the compounds of formulae 28-a, 28-b, 29-a, and 29-b can be masked as esters. Additionally, the hydroxyl groups can be masked as phosphate or phosphonate esters. The hydroxy groups include aliphatic hydroxyl groups, such as those bound to carbons C5, C11, and C15, and phenolic hydroxy groups in the compounds of the invention.

In other embodiments, the invention contemplates solvates of compounds of formulae 28-a, 28-b, 29-a, and 29-b. In general, the term "solvate", when used with reference to a compound, connotes a compound that is associated with one or more molecules of a solvent, such as an organic solvent, inorganic solvent, aqueous solvent or mixtures thereof.

In some embodiments, for example, the compounds of formulae 28-a, 28-b, 29-a, and 29-b exist as hydrates. Hydration can occur during manufacturing of the compounds or compositions comprising the compounds, or the hydration can occur over time, due to the hygroscopic nature of the compounds.

Compounds of the invention can exist as organic solvates as well, including DMF, ether, and alcohol solvates among others. The identification and preparation of any particular solvate falls within the skill of the ordinary artisan of synthetic organic or medicinal chemistry.

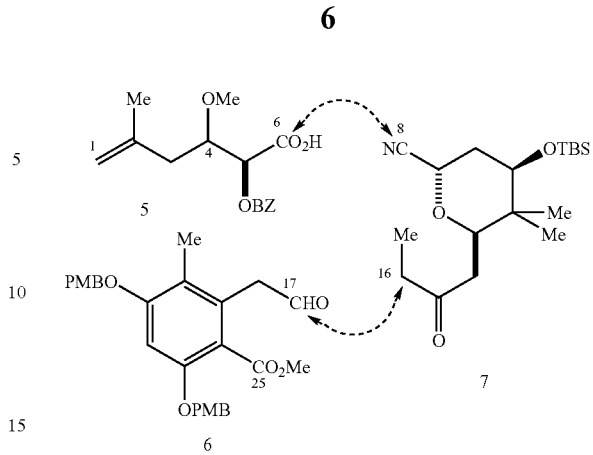

In light of the previously unknown stereochemistry at $C_4$, both anti- and syn-5 were prepared via the sequence shown in Scheme IA below for acid anti-5.

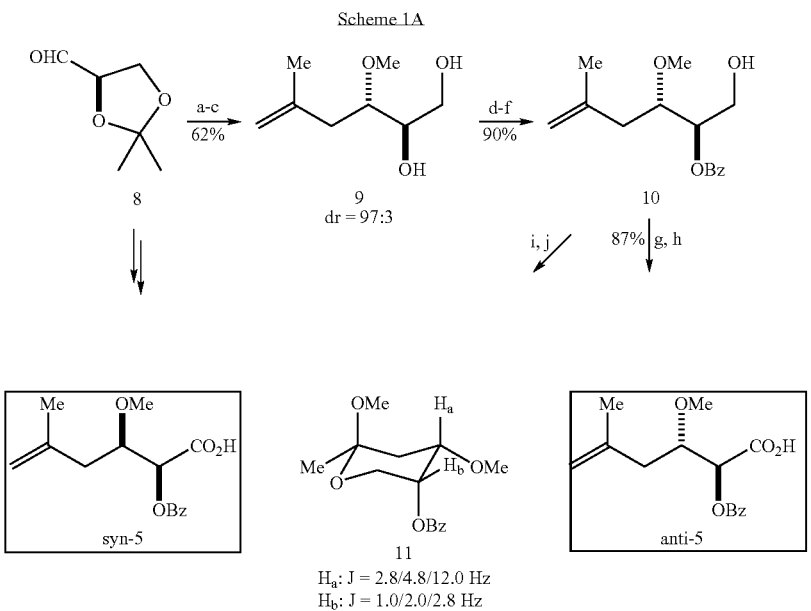

(a) (-)-(Ipc)$_2$BOMe, CH$_2$CMeCH$_2$Li, Et$_2$O, -78° C.; (b) NaH, MeI, THF; (c) PPTS, MeOH/H$_2$O, 50° C.; (d) TBSCl, imid, CH$_2$Cl$_2$; (e) BzCl, py; (f) aq. 3N HCl; (g) Dess-Martin periodinane, CH$_2$Cl$_2$; (h) NaH$_2$PO$_4$, NaClO$_2$, 2-methyl-2-butene, t-BuOH/H$_2$O; (i) O$_3$, CH$_2$Cl$_2$; Me$_2$S; (j) TsOH, CH(OMe)$_3$, MeOH.

General Synthetic Procedures

Compounds of the invention, along with synthetic intermediate compounds, can be prepared according to the processes as described below.

In general, the synthetic approach to making compounds of the invention focused on the coupling of fragments 6-7 via carbon bond-formation to control stereochemistry of the $C_{15}$-$C_{17}$ stereotriad, followed by appending carboxylic acid 5.

Thus, asymmetric methallylation (see Jadhav, P. K.; Bhat et al. *J. Org. Chem.* 1986, 51, 432; acid syn-5 was prepared with antipodal Ipc-borane reagent as described by Evans, D. A. et al. *Tetrahedron Lett.* 1993, 34, 6871) of aldehyde 8, followed by methylation and acetonide hydrolysis, provided diol 9. Diol 9 was converted to benzoate 10 via silylation, benzoylation and desilylation. The relative stereochemistry in compound 10 was confirmed through $^1$H NMR-analysis of acetal 11. Finally, a two-step oxidation of alcohol 10 yielded anti-5 (8 steps, 49% from 8).

Scheme 1B below depicts how the aryl fragment 6 was obtained in 7 steps (41% overall yield) from known aldehyde 12. See Lambooy, J. P., *J. Am. Chem. Soc.* 1956, 78, 771.

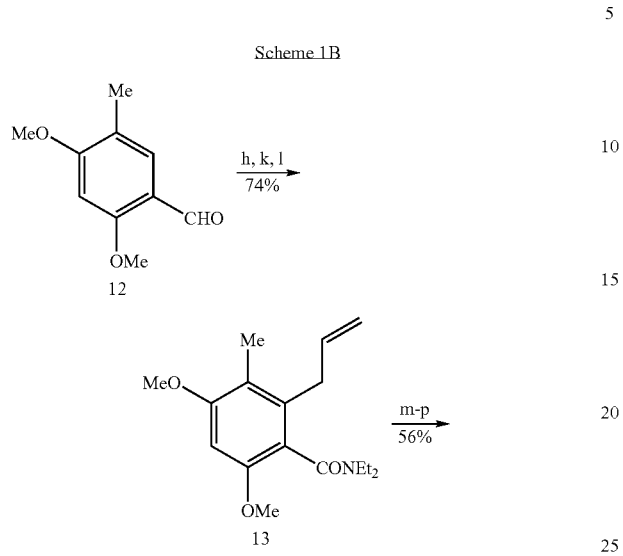

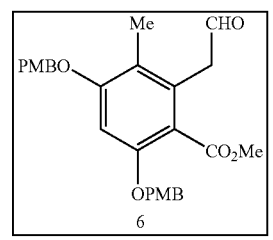

(h) NaH$_2$PO$_4$, NaClO$_2$, 2-methyl-2-butene, t-BuOH/H$_2$O; (i) O$_3$, CH$_2$Cl$_2$; Me$_2$S; (k) SOCl$_2$, benzene; Et$_2$NH; (l) sec-BuLi, CuBr•SMe$_2$, allylBr, THF, -78° C.; (m) BBr$_3$, CH$_2$Cl$_2$, -78→25° C.; (n) Me$_3$OBF$_4$, CH$_2$Cl$_2$; Na$_2$CO$_3$, MeOH; (o) PMBCl, Bu$_4$NI, K$_2$CO$_3$, DMF, 80° C.; (p) cat OsO$_4$, NMO, THF/H$_2$O; NaIO$_4$, aq MeOH.

Thus, compound 12 was subjected to: (1) oxidation/amidation (CHO→CONEt$_2$); (2) ortho-metallation/allylation to give compound 13 (see Kamila, S. et al., *Tetrahedron* 2003, 59, 1339; Casas, R.; et al., *Tetrahedron Lett.* 1995, 36, 1039); (3) BBr$_3$-mediated methyl ether deprotection; (4) methyl ester formation, using a protocol described by Keck, G. E. et al. *Tetrahedron* 2000, 56, 9875; (5) phenol protection; and (6) oxidative double bond cleavage, to give compound 6.

The synthesis of central fragment 7, as depicted in Scheme 1C below, commenced with the preparation of homochiral C$_2$-symmetrical diol 17.

Scheme 1C

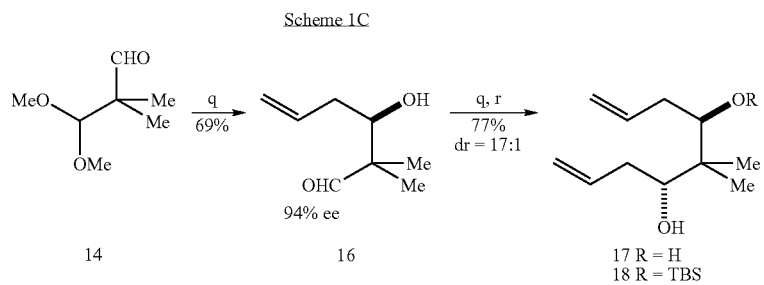

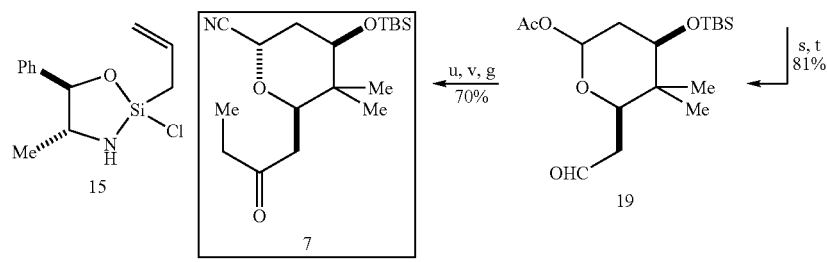

(g) Dess-Martin periodinane, CH$_2$Cl$_2$; (q) 15, PhMe, -15° C.; (r) TBSOTf, 2,6-lutidine, CH$_2$Cl$_2$, 0° C.; (s) O$_3$, CH$_2$Cl$_2$; Ph$_3$P; (t) Ac$_2$O, Et$_3$N, DMAP, CH$_2$Cl$_2$, 0° C.; (u) N,N'-(1R,2R-cyclohexane-1,2-diyl)bis(trifluoromethanesulfonamide), Ti(O$^i$Pr)$_4$, Et$_2$Zn, PhMe, -15° C.; (v) TMSCN, ZnI$_2$, MeCN, 0° C.; aq 1N HCl.

The reaction sequence began with the allylation of monoprotected dialdehyde 14 (see Johnson, P. R. et al., *Org. Chem.* 1984, 49, 4424), using Leighton's silane reagent 15 (Kubota, K. et al., *Angew. Chem. Int. Ed.* 2003, 42, 946), followed by a second allylation of aldehyde 16, which was unmasked during the workup. Monosilylation (18) and ozonolysis destroyed the symmetry and provided a lactol—trapped as acetate 19—that differentiates the chain-termini. Addition of diethylzinc using conditions described by Takahashi, H. et al., *Tetrahedron* 1992, 48, 5691, gave a secondary alcohol, which was oxidized to ketone 7 after acetate displacement with TMSCN (8 steps, 30% from 14).

Scheme 2 depicts below a double convergent coupling strategy that was employed to prepare final compounds 28-a, 28-b, 29-a, and 29-b. Thus, treating the (Z)-chlorophenylboryl enolate derived from 7 with aldehyde 6 yielded one major syn-aldol product 20 that was predicted from an enolate facial bias imposed by the β-alkoxy substituent (Evans. et al., supra).

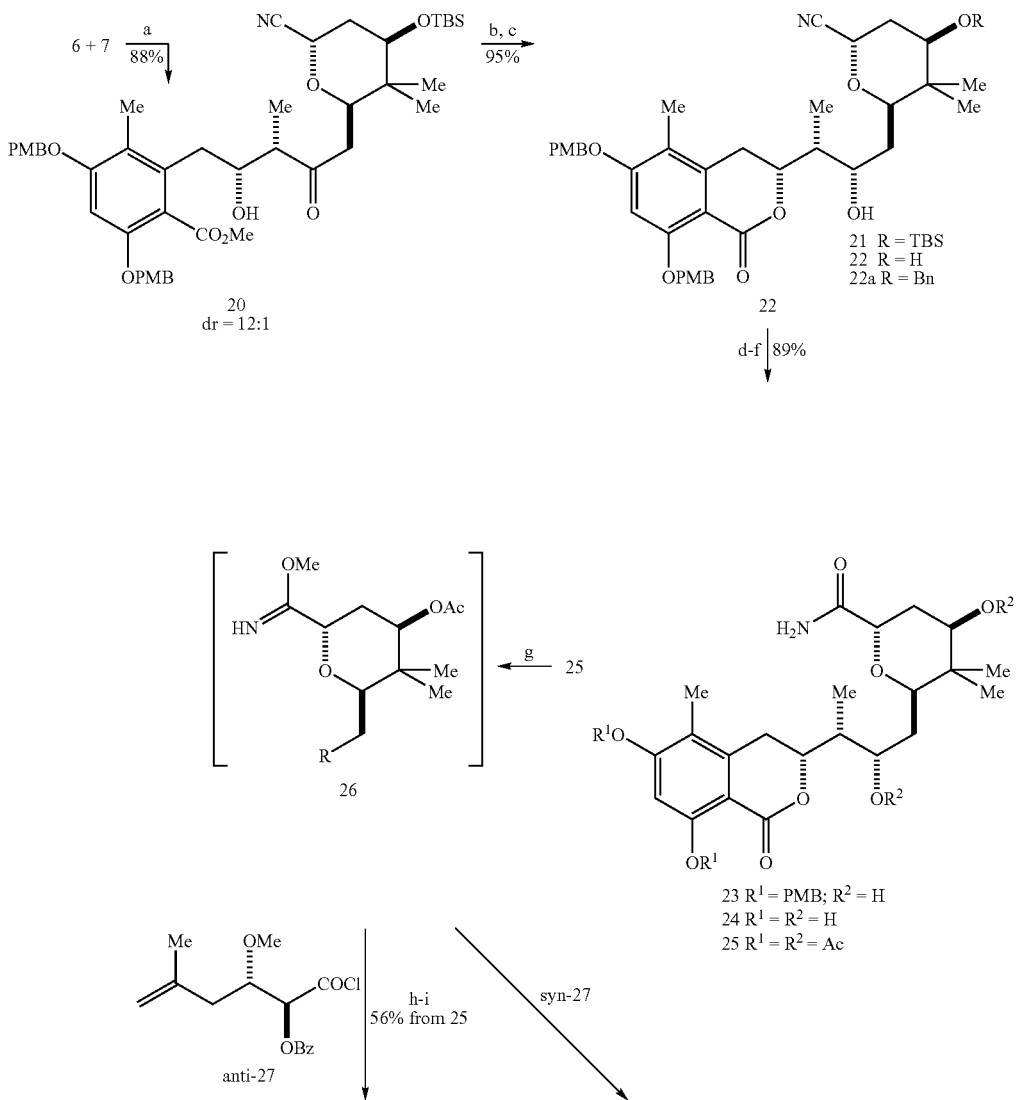

-continued

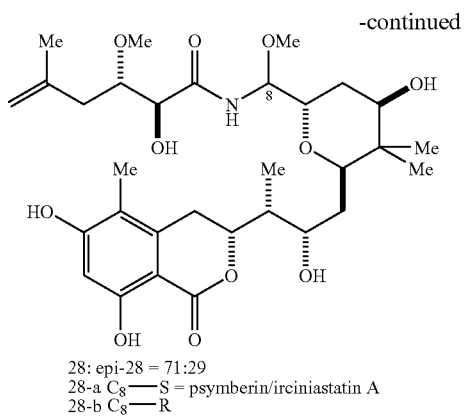

28: epi-28 = 71:29
28-a C8━S = psymberin/irciniastatin A
28-b C8━R

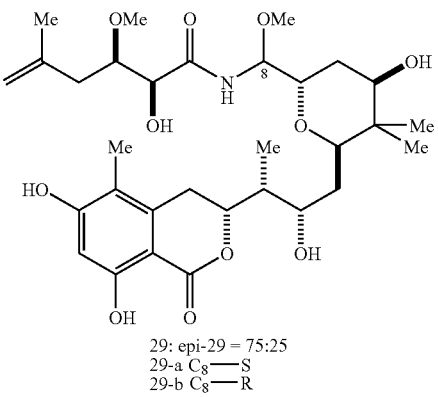

29: epi-29 = 75:25
29-a C8━S
29-b C8━R (a) PhBCl₂, DIPEA, CH₂Cl₂, -78° C.; (b) catecholborane, THF, 0° C.; aq 2N NaOH; (c) TBAF, THF; (d) cat. [PtH(PMe₂OH)(PMe₂O)₂H], EtOH/H₂O, 80° C.; (e) 10% Pd/C, H₂, EtOH; (f) Ac₂O, py; (g) Me₃OBF₄, polyvinylpyridine, CH₂Cl₂; filter; (h) anti- or syn-27, $^i$Pr₂NEt, PhMe, 40° C.; then add NaBH₄, EtOH, 0° C.; (i) LiOH, MeOH.

Reduction of 20 with catecholborane provided lactone 21 directly after basic workup. See Evans, D. A. et al. *J. Org. Chem.* 1990, 55, 5190. (Workup of compound 21 with aqueous Na,K-tartrate, as described in the examples below, allowed the diol to be isolated, for derivatization, as an acetonide derivative, which confirmed the relative 1,2-syn, 2,3-syn stereochemistry at $C_{15}$-$C_{17}$.) Silyl deprotection of 21 gave alcohol 22. Crystallographic analysis of crystals obtained from benzyl ether 22a fully confirmed the assigned structure and relative stereochemistry (FIG. 1). Hydrolysis of the nitrile group in 22 with the platinum(II) catalyst of Ghaffar and Parkins (Ghaffar, T. et al., *Tetrahedron Lett.* 1995, 36, 8657; Ghaffar, T. et al., *J. Mol. Catal. A* 2000, 160, 249) yielded amide 23 in greater than 95% yield. Hydrogenolysis of 23 gave compound 24, and subsequent peracetylation furnished tetraacetate 25 (>90%, 2 steps).

Imidate 26 was generated by a convenient and beneficial procedure by adding polyvinylpyridine during the imidate formation with Me₃OBF₄. After TLC-analysis indicated complete conversion, the reaction mixture was filtered and concentrated, followed by dissolving the crude imidate 26 in toluene, and addition of Hunigs' base and acid chloride 27 (from 5 with (COCl)₂). The mixture was heated to 40° C. for 2 h, cooled to 0° C. and treated with an ethanolic sodium borohydride solution.

After workup, the crude final compounds were saponified to afford a separable mixture of 28-a and 28-b (71:29 ratio) with acid chloride anti-27 (56% from 25), or an inseparable mixture of 29-a and 29-b (75:25 ratio) with syn-27 (50%). Of the 4 diastereomers, only that spectral data ($^1$H, $^{13}$C) recorded for 28 corresponded exactly with psymberin (CD₃OD; Cichewicz, R. H. et al, supra) and irciniastatin A (CDCl₃; obtained by private communication from Profs. Cherry Herald and George Pettit). The rotation of synthetic 28-a ($[α]_D$=+ 25.2, c 0.11, MeOH) agreed with those reported for psymberin ($[α]_D$=+29, c 0.02, MeOH; Cichewicz, R. H. et al, supra) and irciniastatin A ($[α]_D$=+24.4, c 0.55, MeOH; Pettit, G. R. et al., supra).

Processes of Making and Intermediate Compounds

The invention further contemplates processes for making a compound of formula 28-a and certain of its synthetic intermediate compounds, as described above. Still other embodiments provide for those intermediate compounds, as such.

Accordingly, one embodiment relates a process for preparing a compound of formula 28-a:

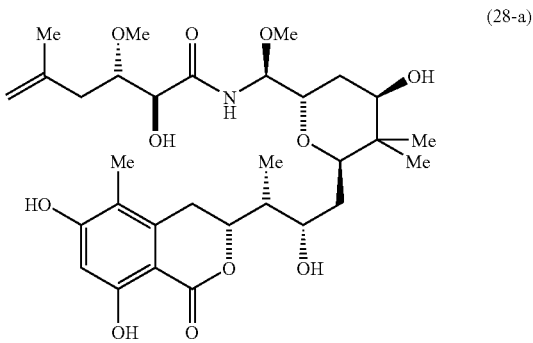

(28-a)

The process comprises the step of reacting a compound of formula 25:

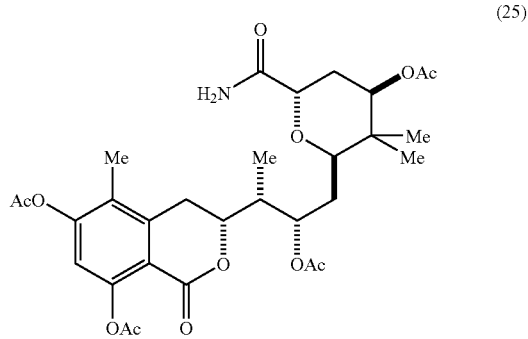

(25)

with a compound of formula anti-27:

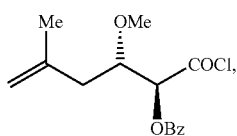

(anti-27)

and then deprotecting, to give the compound having formula 28-a.

The reaction mixture resulting from the process described above may include one or more stereoisomers of a compound of formula 28-a. Thus, in another embodiment, the process further comprises the step of isolating the compound of formula 28-a. The isolation can entail any procedure that is well known to the person who is skilled in the art. Without limitation, exemplary procedures include various kinds of chromatography, such as flash chromatography.

In another embodiment, the invention provides for an intermediate compound having the formula 20:

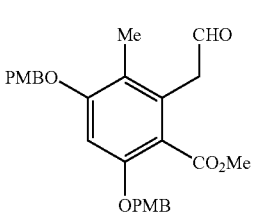

(20)

In still another embodiment, the invention provide a process for preparing the compound of formula 20. The process comprises the step of reacting a compound having the formula 6:

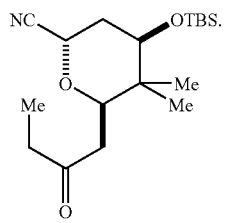

(6)

with a compound having the formula 7:

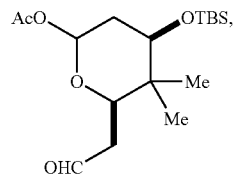

(7)

Other embodiments of the invention relate to the intermediate compound of formula 7. Accordingly, one embodiment is the intermediate compound, which another embodiment is a process for making the intermediate compound of formula 7. The process comprises the steps of:

(a) ethylating a compound of formula 19:

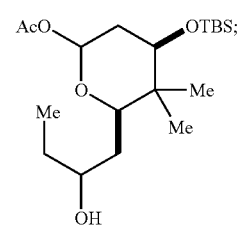

(19)

to give a compound of formula x:

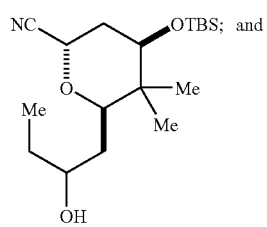

(x)

(b) reacting the compound of formula x with TMSCN to give, and then isolating, a compound of formula xi:

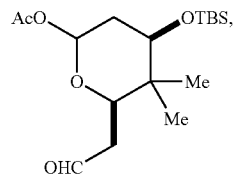

(xi)

(c) oxidizing the compound of formula xi to give the compound of formula 7.

The skill person will recognize that "TBS" in above-described process denotes tert-butyldimethylsilyl. The process can be modified readily to employ other well-known alcohol protecting groups, such as those described in the examples below.

Pharmaceutical Compositions

In other embodiments, the invention provides a pharmaceutical composition comprising a compound of formula 28-a, 28-b, 29-a, or 29-b and a pharmaceutically acceptable carrier. A pharmaceutical composition of the invention may comprise an effective amount of a compound of the invention or an effective dosage amount of a compound of the invention. An effective dosage amount of a compound of the invention includes an amount less than, equal to, or greater than an effective amount of the compound. For example, a pharmaceutical composition in which two or more unit dosages, such as in tablets, capsules and the like, are required to administer an effective amount of the compound, or alternatively, a multi-dose pharmaceutical composition, such as powders, liquids and the like, in which an effective amount of the compound may be administered by administering a portion of the composition.

The pharmaceutical compositions may generally be prepared by a compound of formula 28-a, 28-b, 29-a, or 29-b, including the tautomers, solvates, pharmaceutically acceptable salts, derivatives or prodrugs thereof, with pharmaceutically acceptable carriers, excipients, binders, adjuvants, diluents and the like, to form a desired administrable formulation to treat or ameliorate a neoplastic disease, such as cancer.

Pharmaceutical compositions can be manufactured by methods well known in the art such as conventional granulating, mixing, dissolving, encapsulating, lyophilizing, emulsifying or levigating processes, among others. The compositions can be in the form of, for example, granules, powders, tablets, capsules, syrup, suppositories, injections, emulsions, elixirs, suspensions or solutions.

The instant compositions can be formulated for various routes of administration, for example, by oral administration, by transmucosal administration, by rectal administration, or subcutaneous administration as well as intrathecal, intravenous, intramuscular, intraperitoneal, intranasal, intraocular or intraventricular injection. The compound or compounds of the instant invention can also be administered in a local rather than a systemic fashion, such as injection as a sustained release formulation. One embodiment provides for intravenous administration.

Besides those representative dosage forms described herein, pharmaceutically acceptable excipients and carriers are generally known to those skilled in the art and are thus included in the instant invention. Such excipients and carriers are described, for example, in REMINGTONS PHARMACEUTICAL SCIENCES (Mack Publ. Co. 2000) and in PHARMACEUTICS: THE SCIENCE OF DOSAGE FORM DESIGN, $2^{nd}$ ed. (Churchill Livingstone 2002). The following dosage forms are given by way of illustration and should not be construed as limiting the invention.

For oral, buccal, and sublingual administration, powders, suspensions, granules, tablets, pills, capsules, gelcaps, and caplets can be used as solid dosage forms. These can be prepared, for example, by mixing one or more compounds of the instant invention, or solvates, prodrugs, pharmaceutically acceptable salts or tautomers thereof, with at least one additive or excipient such as a starch or other additive and tableted, encapsulated or made into other desirable forms for conventional administration. Suitable additives or excipients are sucrose, lactose, cellulose sugar, mannitol, maltitol, dextran, sorbitol, starch, agar, alginates, chitins, chitosans, pectins, tragacanth gum, gum arabic, gelatins, collagens, casein, albumin, synthetic or semi-synthetic polymers or glycerides, methyl cellulose, hydroxypropylmethyl-cellulose, and/or polyvinylpyrrolidone. Optionally, oral dosage forms can contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, thickeners, buffers, sweeteners, flavoring agents or perfuming agents. Additionally, dyestuffs or pigments may be added for identification. Tablets and pills may be further treated with suitable coating materials known in the art.

Liquid dosage forms for oral administration may be in the form of pharmaceutically acceptable emulsions, syrups, elixirs, suspensions, slurries and solutions, which may contain an inactive diluent, such as water. Pharmaceutical formulations may be prepared as liquid suspensions or solutions using a sterile liquid including but not limited to an oil, water, an alcohol, and combinations of these. Pharmaceutically suitable surfactants, suspending agents, emulsifying agents, and the like may be added for oral or parenteral administration.

For nasal administration, the pharmaceutical compositions may be a spray or aerosol containing an appropriate solvent and optionally other compounds such as, but not limited to, stabilizers, antimicrobial agents, antioxidants, pH modifiers, surfactants, bioavailability modifiers and combinations of these. A propellant for an aerosol formulation may include compressed air, nitrogen, carbon dioxide, or a hydrocarbon based low boiling solvent. The compound or compounds of the instant invention are conveniently delivered in the form of an aerosol spray presentation from a nebulizer or the like.

Injectable dosage forms for parenteral administration generally include aqueous suspensions or oil suspensions, which may be prepared using a suitable dispersant or wetting agent and a suspending agent. Injectable forms may be in solution phase or a powder suitable for reconstitution as a solution. Both are prepared with a solvent or diluent. One embodiment of the invention, for example, provides for a lyophilized powder of the pharmaceutical composition. Acceptable solvents or vehicles include sterilized water, Ringer's solution, or an isotonic aqueous saline solution. Alternatively, sterile oils may be employed as solvents or suspending agents. Typically, the oil or fatty acid is non-volatile, including natural or synthetic oils, fatty acids, mono-, di- or tri-glycerides. In one embodiment, for example, the pharmaceutically acceptable carrier comprises polyethylene glycol and saline solution.

For injection, the formulations may optionally contain stabilizers, pH modifiers, surfactants, bioavailability modifiers and combinations of these. The compounds may be formulated for parenteral administration by injection such as by bolus injection or continuous infusion. A unit dosage form for injection may be in ampoules or in multi-dose containers.

For rectal administration, the pharmaceutical formulations may be in the form of a suppository, an ointment, an enema, a tablet or a cream for release of compound in the intestines, sigmoid flexure and/or rectum. Rectal suppositories are prepared by mixing one or more compounds of the instant invention, or pharmaceutically acceptable salts or tautomers of the compound, with acceptable vehicles, for example, cocoa butter or polyethylene glycol, which is solid phase at room temperature but liquid phase at those temperatures suitable to release a drug inside the body, such as in the rectum. Various other agents and additives may be used in the preparation of suppositories as is well known to those of skill in the art.

The formulations of the invention may be designed to be short-acting, fast-releasing, long-acting, and sustained-releasing as described below. Thus, the pharmaceutical formulations may also be formulated for controlled release or for slow release. The instant compositions may also comprise, for example, micelles or liposomes, or some other encapsulated form, or may be administered in an extended release form to provide a prolonged storage and/or delivery effect. Therefore, the pharmaceutical formulations may be compressed into pellets or cylinders and implanted intramuscularly or subcutaneously as depot injections or as implants such as stents. Such implants may employ known inert materials such as silicones and biodegradable polymers.

Specific dosages may be adjusted depending on conditions of disease, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant invention.

A therapeutically effective dose may vary depending upon the route of administration and dosage form. Typically, the compound or compounds of the instant invention are selected to provide a formulation that exhibits a high therapeutic index. The therapeutic index is the dose ratio between toxic and therapeutic effects which can be expressed as the ratio between $LD_{50}$ and $ED_{50}$. The $LD_{50}$ is the dose lethal to 50% of the population and the $ED_{50}$ is the dose therapeutically effective in 50% of the population. The $LD_{50}$ and $ED_{50}$ are determined by standard pharmaceutical procedures in animal cell cultures or experimental animals.

The dosage regimen for neoplastic diseases as described more fully below with the compounds of this invention and/or compositions of this invention is based on a variety of factors, including the type of disease, the age, weight, sex, medical condition of the patient, the severity of the condition, the route of administration, and the particular compound employed. Thus, the dosage regimen may vary widely, but can be determined routinely using standard methods. In general, dosage levels of the order from about 0.01 mg to 30 mg per kilogram of body weight per day, for example from about 0.1 mg to 10 mg/kg, or from about 0.25 mg to 1 mg/kg are useful for all methods of use disclosed herein. In one embodiment, the dosage is about 0.1 to about 2.0 mg/kg. For example, compound 28-a can be administered at dosages within this range. In another embodiment, the dosage is about 0.1 to about 30 mg/kg, which is illustrative of dosages for compounds 28-b, 29-a, and 29-b.

For oral administration, the pharmaceutical composition may be in the form of, for example, a capsule, a tablet, a suspension, or liquid. The pharmaceutical composition can be made in the form of a dosage unit containing a given amount of the active ingredient. For example, these may contain an amount of active ingredient from about 1 to 2000 mg, for example from about 1 to 500 mg, or from about 5 to 150 mg. A suitable daily dose for a human or other mammal may vary widely depending on the condition of the patient and other factors, but, once again, can be determined using routine methods.

As noted above, the compounds, pharmaceutically acceptable salts, tautomer, solvates, and prodrugs of this invention may also be administered by injection as a composition with suitable carriers including saline, dextrose, or water. The daily parenteral dosage regimen can range from about 0.1 to about 30 mg/kg of total body weight, such as from about 0.1 to about 10 mg/kg, or from about 0.25 mg to 1 mg/kg.

Formulations suitable for topical administration include liquid or semi-liquid preparations suitable for penetration through the skin (e.g., liniments, lotions, ointments, creams, or pastes) and drops suitable for administration to the eye, ear, or nose.

Topical doses of a compound of the invention can be from 0.1 mg to 150 mg administered from one to four, for example one or two times daily. For topical administration, the active ingredient can comprise from 0.001% to 10% w/w, e.g., from 1% to 2% by weight of the formulation, although it can comprise as much as 10% w/w, but typically not more than 5% w/w. In one embodiment, the concentration is from 0.1% to 1% of the formulation.

The pharmaceutical compositions can be subjected to conventional pharmaceutical operations such as sterilization and/or may contain adjuvants, such as preservatives, stabilizers, wetting agents, emulsifiers, buffers, etc. The pharmaceutically active compounds of this invention can be processed in accordance with conventional methods of pharmacy to produce medicinal agents for administration to patients, including humans and other mammals.

Method of Treatment

The invention also provides, as another embodiment, a method for treating a neoplastic disease in a subject. For the treatment of such diseases, the compounds of the present invention can be administered in therapeutically effective amounts by several different modes, including without limitation, oral, parental, by spray inhalation, rectal, or topical, as discussed above. The term "parenteral" is used here to encompass subcutaneous, intravenous, intramuscular, and intrasternal administration, as well as infusion techniques and intraperitoneal administration.

Treatment of diseases and disorders herein is intended to also include therapeutic administration of a compound of the invention (or a pharmaceutical salt, solvate or prodrug thereof) or a pharmaceutical composition containing the compound to a subject believed to be in need of preventative treatment, e.g., for pain, inflammation, and the like. A subject can include but is not limited to an animal, such as a mammal, including a human.

Treatment also encompasses administration of the compound or pharmaceutical composition to subjects not having been diagnosed as having a need thereof, i.e., prophylactic administration to the subject. Generally, the subject is initially diagnosed by a licensed physician and/or authorized medical practitioner, and a regimen for prophylactic and/or therapeutic treatment via administration of the compound(s) or compositions of the invention is suggested, recommended or prescribed.

"Treating" or "treatment of" within the context of the instant invention denotes an alleviation, in whole or in part, of symptoms associated with a disorder or disease, or halt of further progression or worsening of those symptoms, or prevention or prophylaxis of the disease or disorder. Similarly, as used herein, an "effective amount" or "therapeutically effective amount" of a compound of the invention refers to an amount of the compound that alleviates, in whole or in part, symptoms associated with a disorder or disease, or halts of further progression or worsening of those symptoms, or prevents or provides prophylaxis for the disease or disorder. For example, within the context of treating patients suffering from a neoplastic disease, successful treatment can include a reduction in tumor adhesion and anchorage; an alleviation of symptoms related to a cancerous growth or tumor, or proliferation of diseased tissue; a halting in the progression of a disease such as cancer or in the growth of cancerous cells. Exemplary neoplastic diseases that can be treated by the compounds or pharmaceutical compositions of this invention include but are not limited to pancreatic cancer, bladder cancer, breast cancer, lung cancer, colon cancer, prostate cancer, brain cancer, ovarian cancer, cervical cancer, gastrointestinal cancer, head cancer, neck cancer, and leukemia.

While it may be possible to administer a compound of the invention alone in the methods described, the compound administered is generally present as an active ingredient in a desired dosage unit formulation, such as pharmaceutically acceptable composition containing conventional pharmaceutically acceptable carriers as described above.

The following examples are proffered merely to illustrate the invention described above; they are not intended to limit in any way the scope of this invention.

General Synthetic Details

Unless otherwise noted, commercially available materials were used without further purification. All solvents were of HPLC or ACS grade. Solvents used for moisture sensitive operations were distilled from drying reagents under a nitrogen atmosphere: $Et_2O$ and THF from sodium benzophenone ketyl; benzene and toluene from sodium; $CH_2Cl_2$ from $CaH_2$, pyridine over solid KOH, anhydrous N,N-dimethylformamide, and $CH_3CN$ were purchased from commercial sources. Reactions were performed under an atmosphere of nitrogen with magnetic stirring unless noted otherwise. Flash chromatography (FC) was performed using E Merck silica gel 60 (240-400 mesh) according to the protocol of Still, Kahn, and Mitra (*J. Org. Chem.* 1978, 43, 2923). Thin layer chromatography was performed performed using precoated plates purchased from E. Merck (silicagel 60 PF254, 0.25 mm) that were visualized using a $KMnO_4$ or Ce (IV) stain.

Nuclear magnetic resonance (NMR) spectra were recorded on a Varian Inova-400 or Mercury-300 spectrometer at operating frequencies of 400/300 MHz ($^1$H NMR) or 100/75 MHz ($^{13}$C NMR). Chemical shifts (δ) are given in ppm relative to residual solvent (usually chloroform δ 7.26 for $^1$H NMR or δ 77.23 for proton decoupled $^{13}$C NMR), and coupling constants (J) in Hz. Multiplicity is tabulated as s for singlet, d for doublet, t for triplet, q for quadruplet, and m for multiplet, whereby the prefix app is applied in cases where the true multiplicity is unresolved, and br when the signal in question is broadened.

Infrared spectra were recorded on a Perkin-ElmerI 1000 series FTIR with wavenumbers expressed in $cm^{-1}$ using samples prepared as thin films between salt plates. Electrospray ionization mass spectra (ESI-MS) were recorded on a Shimadzu 2010-LCMS. Optical rotations were measured at 20° C. on a Rudolph Research Analytical Autopole® IV polarimeter.

EXAMPLE 1

Preparation of Compound (i)

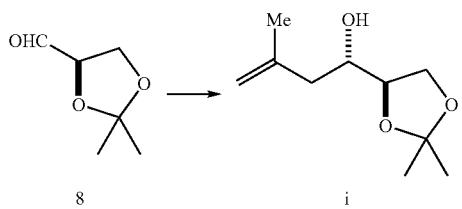

To a round bottom flask containing TMEDA (3.03 mL, 20.00 mmol) and n-BuLi (2.5 M in hexane, 8.0 mL, 20 mmol) in $Et_2O$ (12 mL) was added under $N_2$ and at −78° C. 2-methylpropene (3.40 g, 60.00 mmol). The reaction was allowed to stir at −78° C. for 1 h and at room temperature overnight. The mixture obtained was added to a stirred solution of (−)-(Ipc)$_2$BOMe (6.34 g, 20.00 mmol) in $Et_2O$ (20 mL) at −78° C. After stirring at −78° C. for 1 h and at room temperature for 1 h, the reaction was cooled to −78° C. and a solution of aldehyde 8 (Ahrendt, K. A.; Williams, R. M. *Org. Lett.* 2004, 6, 4539) (2.60 g, 20.00 mmol) in $Et_2O$ (34 mL) was added dropwise. After 1 h, the reaction was quenched by adding pH 7 buffer (120 mL), MeOH (120 mL) and 30% $H_2O_2$ (60 mL), and stirred at room temperature for 30 min. The crude was extracted with $Et_2O$ and the combined organic phases were washed with water and dried over $MgSO_4$. After concentration, the residue obtained was purified by FC (silica gel; EtOAc/hexanes 1:4) to give allylic alcohol i 2.6 g (70%, dr 95:5) as a colorless oil contaminated with isopinocampheol, and was used without further purification. $[α]_D$=+16.38 ($CHCl_3$, c=1.0); $^1$H NMR (CDCl3) δ 1.37 (s, 3H), 1.44 (s, 3H), 1.78 (s, 3H), 2.01 (d, 1H, J=2.4 Hz), 2.11 (dd, 1H, J=9.4, 14.2 Hz), 2.30 (dd, 1H, J=4.0, 14.2 Hz), 3.85 (m, 1H), 4.00 (m, 3H), 4.82 (s, 1H), 4.89 (s, 1H); $^{13}$C NMR (CDCl3) δ 22.3, 25.3, 26.6, 41.7, 65.4, 68.8, 78.4, 109.1, 113.7, 141.9; IR $ν_{max}$ 3477, 1219, 1066 $cm^{-1}$; MS (ES) m/z: 209.05 ([MNa]$^+$).

EXAMPLE 2

Preparation of Compound (ii)

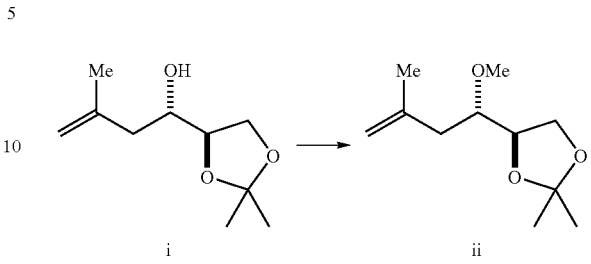

To a suspension of NaH (60% in mineral oil, 620 mg, 15.4 mmol) in THF (70 mL) was added a solution of allylic alcohol i (2.6 g, 13.98 mmol; Example 1) in THF (14 mL) at 0° C. After stirring at 0° C. for 30 min, MeI (1.05 mL, 16.77 mmol) was added and the reaction was allowed to stir at ambient temperature overnight. The crude was extracted with $Et_2O$ and the combined organic phases were dried over $MgSO_4$, filtered and concentrated. The residue obtained was purified by FC (silica gel, $Et_2O$/Hexanes 1:1) to afford methyl ether ii 2.52 g (90%) as a colorless volatile oil. $[α]_D$=+1.92 ($CHCl_3$, c=1.0); $^1$H NMR (CDCl$_3$) δ 1.35 (s, 3H), 1.43 (s, 3H), 1.80 (s, 3H), 2.22 (m, 2H), 3.45 (s, 3H), 3.47 (m, 1H), 3.90 (dd, 1H, J=6.4, 7.6 Hz), 4.02 (app t, 1H, J=6.8 Hz), 4.06 (app q, 1H, J=6.4 Hz), 4.80 (d, 1H, J=0.8 Hz), 4.83 (s, 1H); $^{13}$C NMR (CDCl$_3$) δ 22.9, 25.3, 26.5, 39.5, 58.8, 65.8, 77.5, 79.7, 109.0, 113.0, 142.4; IR $ν_{max}$ 1219, 1104, 1078 $cm^{-1}$; MS (ES) m/z: 223.05 ([MNa]$^+$).

EXAMPLE 3

Preparation of Compound (9)

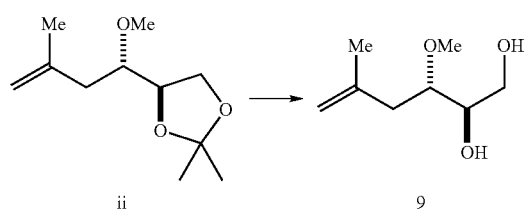

A mixture of the methyl ether ii (1.53 g, 7.65 mmol; Example 2), PPTS (408 mg, 1.63 mmol), and water (2.55 mL) in MeOH (40 mL) was stirred at 50° C. overnight and then brought to room temperature. $NaHCO_3$ (600 mg, 7.14 mmol) was added and solvent was removed under reduced pressure. The residue obtained was dissolved in EtOAc (50 mL), dried with $MgSO_4$, filtered and concentrated. The residue obtained was purified by FC (silica gel, EtOAc) to afford 1.13 g (93%) of compound 9 as colorless oil. $[α]^{24}_D$=+29.0 (EtOAc, c=0.29); $^1$H NMR (CDCl$_3$) δ 1.78 (s, 3H), 2.17 (dd, 1H, J=6.0, 14.4 Hz), 2.36 (dd, 1H, J=6.9, 14.4 Hz), 2.53 (bs, 1H), 2.58 (bs, 1H), 3.41 (s, 3H), 3.52 (m, 1H), 3.68 (m, 2H), 3.77 (ddd, 1H, J=1.2, 6.3, 12.0 Hz), 4.79 (bs, 1H), 4.83 (t, 1H, J=1.5 Hz); $^{13}$C NMR (CDCl$_3$) δ 22.7, 38.7, 58.3, 63.0, 72.3, 81.8, 113.3, 142.2; IR $ν_{max}$ 3391, 2919, 1646, 1448, 1094 $cm^{-1}$; MS (ES) m/z: 183.00 ([MNa]$^+$).

EXAMPLE 4

Preparation of Compound (iii)

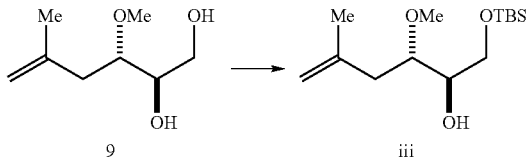

To a solution of compound 9 (640 mg, 4.0 mmol) and imidazole (408 mg, 6.0 mmol) in CH$_2$Cl$_2$ (15 mL) was added TBSCl (724 mg, 4.8 mmol) in CH$_2$Cl$_2$ (3 mL) at 0° C. After 30 min, the reaction mixture was washed with sat. NaHCO$_3$ and water and dried over MgSO$_4$. After concentration, the residue was purified by FC (silica gel, hexanes/EtOAc, 10:1) to give iii 1.04 g (95%) as colorless oil. $[\alpha]^{22}{}_D$=+8.57 (EtOAc, c=0.28); $^1$H NMR (CDCl$_3$) δ 0.08 (s, 3H), 0.08 (s, 3H), 0.90 (s, 9H), 1.80 (s, 3H), 2.30 (m, 2H), 2.45 (d, 1H, J=3.3 Hz), 3.40 (s, 3H), 3.42 (m, 1H), 3.69 (m, 3H), 4.81 (m, 2H); $^{13}$C NMR (CDCl$_3$) δ -5.4, 18.3, 22.9, 25.9, 38.5, 58.2, 63.4, 72.7, 79.9, 112.7, 142.9; IR $v_{max}$ 3468, 1650, 1463, 1255, 1103 cm$^{-1}$; MS (ES) m/z: 297.10 ([MNa]$^+$).

EXAMPLE 5

Preparation of Compound (10)

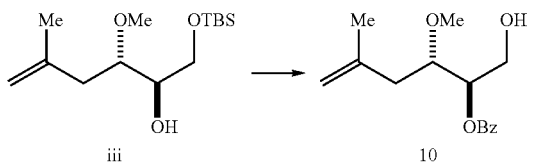

To a solution of iii (1.00 g, 3.65 mmol) in pyridine (8 mL) was added benzoyl chloride (1.69 mL, 7.30 mmol). After 30 min at room temperature, benzoyl chloride (0.56 mL, 2.43 mmol) was added again and stirred for another 30 min. Sat. NaHCO$_3$ solution was added and the crude was extracted with EtOAc. The combined organic extracts were washed with 1 N HCl and water and concentrated. 3N HCl (6 mL) was added to a solution of the crude benzoate in THF (30 mL). After stirring at room temperature for 2 h, NaHCO$_3$ (2.0 g) was added and the solvent was removed under reduced pressure. The residue obtained was extracted with CH$_2$Cl$_2$ and the combined organic extracts were washed with water and dried over MgSO$_4$. After removal of solvent, the residue was purified by FC (silica gel, hexanes/EtOAc, 3:1) to give compound 10 (914 mg, 95%) as colorless oil. $[\alpha]^{24}{}_D$=-26.4 (EtOAc, c=0.55); $^1$H NMR (CDCl$_3$) δ 1.81 (s, 3H), 2.30 (dd, 1H, J=6.0, 14.4 Hz), 2.42 (dd, 1H, J=7.5, 14.4 Hz), 3.49 (s, 3H), 3.80 (ddd, 1H, J=3.9, 6.0, 7.5 Hz), 3.92 (dd, 1H, J=3.9, 12.0 Hz), 3.97 (dd, J=4.8, 12.0 Hz), 4.80 (m, 1H), 4.84 (m, 1H), 5.13 (ddd, 1H, J=3.9, 3.9, 4.8 Hz), 7.45 (m, 2H), 7.58 (m, 1H), 8.07 (m, 2H); $^{13}$C NMR (CDCl$_3$) δ 22.6, 39.6, 58.9, 61.8, 76.2, 80.2, 113.5, 128.4, 129.7, 129.9, 133.2, 141.6, 166.3; IR $v_{max}$ 3439, 2918, 1715, 1250, 1272, 1114 cm$^{-1}$; MS (ES) m/z: 287.00 ([MNa]$^+$), 319.05 ([MNa+MeOH]$^+$).

EXAMPLE 6

Preparation of Compound (11)

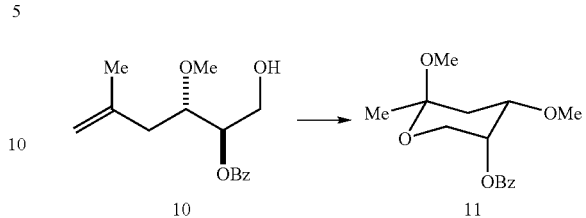

Ozone was bubbled through a solution of compound 10 (30 mg, 114 μmol) in CH$_2$Cl$_2$ (10 mL) at -78° C. until the solution became slightly blue. Me$_2$S (1 mL) was added and the resultant solution was stirred at room temperature overnight. After removal of solvent, the residue obtained was purified by FC (silica gel; hexanes/EtOAc, 1:1) to give a mixture of four hemiketals (24 mg, 89%) as viscous oil. To a solution of hemiketals (24 mg, 90 μmol) in MeOH (3 mL) was added HC(OMe)$_3$ (0.2 mL) and a catalytic amount of pTsOH. After stirring at room temperature for 1 h, Et$_3$N (50 μL) was added and stirred for 5 min. The solvent was removed under reduced pressure and the residue obtained was purified by FC (silica gel; hexanes/EtOAc, 3:1) to give compound 11 (20 mg, 80%) as a colorless oil. $^1$H NMR (CDCl$_3$) δ 1.42 (s, 3H), 1.96 (dd, 1H, J=12.0, 12.4 Hz), 2.06 (dd, 1H, J=4.8, 12.4 Hz), 3.23 (s, 3H), 3.37 (s, 3H), 3.75 (dd, 1H, J=1.0, 12.8 Hz), 3.81 (ddd, 1H, J=2.8, 4.8, 12.0 Hz), 3.92 (dd, 1H, J=2.0, 12.8 Hz), 5.44 (ddd, 1H; J=1.0, 2.0, 2.8 Hz), 7.44 (t, 2H, J=7.6 Hz), 7.56 (t, 1H, J=7.6 Hz), 8.08 (d, 2H, J=7.6 Hz); $^{13}$C NMR (CDCl$_3$) δ 23.3, 37.2, 48.2, 56.1, 62.3, 66.5, 73.3, 99.7, 128.3, 129.8, 133.0, 166.2; MS (ES) m/z: 303.00 ([MNa]$^+$).

EXAMPLE 7

Preparation of Compound (anti-5)

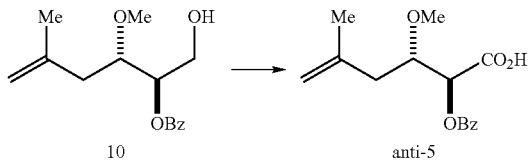

To a mixture of 10 (115 mg, 435 μmol) and NaHCO$_3$ (73 mg, 870 μmol) in CH$_2$Cl$_2$ (6 mL) was added Dess-Martin Periodinane (369 mg, 870 μmol) at 0° C. After stirring 1 h at room temperature, ether (20 mL) and 10% Na$_2$S$_2$O$_3$ (10 mL) was added. After 5 min, the organic layer was separated and washed thoroughly with sat. NaHCO$_3$ and water and dried over MgSO$_4$. Filtration and concentration afforded the crude aldehyde. To a mixture of the crude aldehyde, t-BuOH (13 mL), water (3.3 mL) and 2-methyl-2-butene (3.3 mL) was added NaH$_2$PO$_4$ (197 mg, 1.43 mmol) and NaClO$_2$ (197 mg, 1.74 mmol) at 0° C. After stirring at room temperature for 1.5 h, EtOAc (30 mL) and 0.05 N NaHSO$_4$ (30 mL) was added. After 5 min, the crude was extracted with EtOAc and the combined organic extracts were washed with water and dried over MgSO$_4$. After concentration, the residue was purified by column chromatography (silica gel, MeOH/CH$_2$Cl$_2$, 1:5) to give anti-5 (105 mg, 87%) as a viscous oil. $[\alpha]^{22}{}_D$=-13.6

(EtOAc, c=0.36); $^1$H NMR (CDCl$_3$) δ 1.68 (s, 3H), 2.31 (dd, 1H, J=3.6, 14.0 Hz), 2.41 (dd, 1H, J=8.4, 14.0 Hz), 3.45 (s, 3H), 3.86 (m, 1H), 4.76 (bs, 2H), 5.45 (bs, 1H), 7.38 (m, 2H), 7.52 (m, 1H), 8.02 (m, 2H); $^{13}$C NMR (CDCl$_3$) δ 22.5, 38.7, 57.9, 73.7, 79.5, 113.0, 128.2, 129.4, 129.9, 133.2, 141.8, 166.1, 174.2; IR ν$_{max}$ 3438, 2918, 1726, 1601, 1273, 1116 cm$^{-1}$; MS (ES) m/z: 301.00 ([MNa]$^+$).

EXAMPLE 8

Preparation of Compound (syn-5)

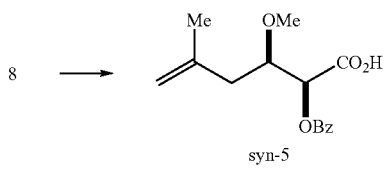

syn-5

Syn-5 was synthesized form aldehyde 8 using the similar procedure as the synthesis of anti-5, but starting with enantiomeric borane ((+)-(Ipc)$_2$BOMe). $^1$H NMR (CDCl$_3$) δ 1.75 (s, 3H), 2.33 (dd, 1H, J=7.8, 13.8 Hz), 2.45 (dd, 1H, J=6.6, 13.8 Hz), 3.42 (s, 3H), 4.04 (ddd, 1H, J=2.1, 6.6, 7.8 Hz), 4.68 (bs, 1H), 4.79 (t, 1H, J=1.5 Hz), 5.25 (d, 1H, J=2.1 Hz), 7.42 (m, 2H), 7.55 (m, 1H), 8.09 (m, 2H); $^{13}$C NMR (CDCl$_3$) δ 22.5, 38.2, 58.2, 73.3, 78.8, 114.1, 128.4, 129.2, 129.9, 133.3, 140.9, 166.1, 172.9; IR ν$_{max}$ 3446, 2938, 1726, 1602, 1266, 1107, 1072 cm$^{-1}$; MS (ES) m/z: 301.00 ([MNa]$^+$).

EXAMPLE 9

Preparation of Compound (iv)

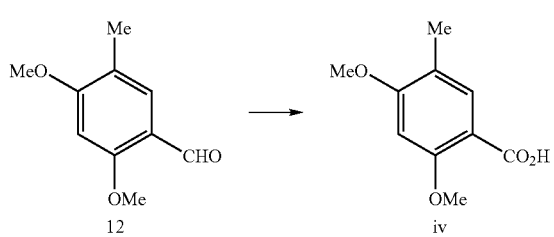

To a solution of benzaldehyde 12 (Lambooy, J. P. *J. Am. Chem. Soc.* 1956, 78, 771) (4.19 g, 23.28 mmol) in DMSO (67 mL) were added NaH$_2$PO$_4$ (8.03 g, 58.20 mmol) in H$_2$O (9 mL) and NaClO$_2$ (5.26 g, 46.56 mmol) in H$_2$O (33 mL) at 10° C. After stirring overnight at room temperature, sat Na$_2$CO$_3$ (200 mL) was added. After 5 min, the crude was extracted with EtOAc (100 mL) and the aqueous phase was acidified with conc. HCl to pH 2. The white precipitate that formed was collected by filtration to give acid iv (3.88 g, 85%). $^1$H NMR (CDCl$_3$) δ 2.16 (s, 3H), 3.92 (s, 3H), 4.07 (s, 3H), 6.46 (s, 1H), 7.91 (1H, d, J=0.8 Hz), 10.61 (br, 1H); $^{13}$C NMR (CDCl$_3$) δ 15.1, 55.6, 56.7, 94.1, 108.8, 120.6, 134.7, 158.2, 162.9, 165.6,; IR ν$_{max}$ 3242, 1725, 1621, 1280, 1021, 828 cm$^{-1}$; MS (ES) m/z: 197.05 ([MH]$^+$), 219.00 ([MNa]$^+$).

EXAMPLE 10

Preparation of Compound (v)

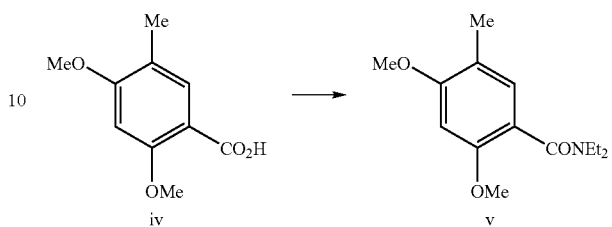

To a solution of benzoic acid iv (3.88 g, 19.79 mmol) in benzene (110 mL) was added dropwise thionyl chloride (8.52 mL, 77 mmol) at room temperature. The reaction mixture was cooled down after refluxing for 2 h. The solvent and excess of thionyl chloride were removed under reduce pressure to give crude acid chloride. To a solution of crude acid chloride in benzene (56 mL) was added dropwise diethylamine (6.14 mL, 59.38 mmol) at 0° C. After stirring 2 h at 0° C. and overnight at room temperature, the reaction was concentrated and the crude oil was purified by FC (silica gel, EtOAc/Hexanes/NEt$_3$ 9:1:0.05) to afford compound v (4.82 g, 97%). $^1$H NMR (CDCl$_3$) δ 1.03 (t, 3H, J=7.2 Hz), 1.23 (t, 3H, J=7.2 Hz), 2.13 (s, 3H), 3.17 (q, 2H, J=7.2 Hz), 3.55 (q, 2H, J=7.2 Hz), 3.81 (s, 3H), 3.85 (s, 3H), 6.41 (s, 1H), 6.95 (s, 1H); $^{13}$C NMR (CDCl$_3$) δ 12.9, 14.0, 15.2, 38.8, 42.8, 55.4, 55.9, 95.0, 118.5, 118.6, 129.2, 154.5, 158.7, 169.0; IR ν$_{max}$ 1614, 1462, 1207, 1143, 1033 cm$^{-1}$; MS (ES) m/z: 252.10 ([MH]$^+$).

EXAMPLE 11

Preparation of Compound (13)

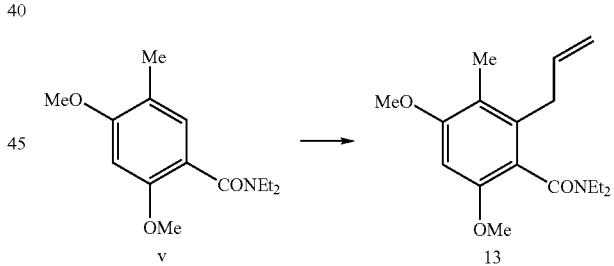

To a solution of amide v (1.61 g, 6.40 mmol) in THF (16 mL) was added sec-BuLi (1.4 M in cyclohexane, 10.06 mL, 14.09 mmol) at −78° C. dropwise. After 1 h at −78° C., CuBr.Me$_2$S (2.63 g, 12.81 mmol) was added and the reaction was allowed to warm to −15° C. After 30 min, allylbromide (1.12 mL, 12.81 mmol) was added at −78° C. and kept at this temperature for 1 h. The reaction was warmed to room temperature, filtered through a pad of silica gel and washed with EtOAc. The filtrate was dried over MgSO$_4$, concentrated and purified by FC (silica gel, EtOAc/Hexanes/NEt$_3$ 85:15:0.5) to give (1.41 g, 76%) of compound 13. $^1$H NMR (CDCl$_3$) δ 1.02 (t, 3H, J=6.8 Hz), 1.23 (t, 3H, J=7.2 Hz), 2.09 (s, 3H), 3.04 (dt, 1H, J=7.6 Hz), 3.15 (dt, 1H, J=7.6 Hz), 3.24-3.40 (3H, m), 3.79 (s, 3H), 3.84 (s, 3H), 4.97 (m, 2H), 5.84 (m, 1H), 6.36 (m, 1H); $^{13}$C NMR (CDCl$_3$) δ 10.8, 12.5, 13.5, 34.7, 38.1, 42.7, 55.4, 55.5, 93.2, 115.3, 117.9, 119.2, 135.4, 136.1, 154.0, 158.3, 168.5; IR (film) 1626, 1594, 1460, 1436, 1318, 1207, 1140, 1094 cm$^{-1}$; MS (ES) m/z: 292.10 ([MH]$^+$).

EXAMPLE 12

Preparation of Compound (vi)

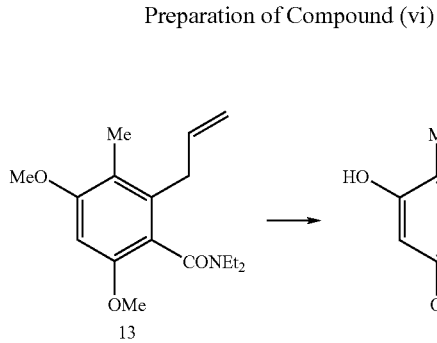

To a solution of 13 (1.00 g, 3.61 mmol) in CH$_2$Cl$_2$ (60 mL) was added a solution of BBr$_3$ (2.05 mL, 21.7 mmol) in CH$_2$Cl$_2$ (20 mL) at −78° C. After stirring at −78° C. for 30 min, 0° C. for 4 h and 25° C. for 1 h, water was added at 0° C. and the crude was extracted with CH$_2$Cl$_2$. The combined extracts were washed with water, dried over MgSO$_4$ and concentrated. The residue obtained was purified by FC (silica gel; CH$_2$Cl$_2$/EtOAc, 20:1) to give vi (730 mg, 81%) as white solid: $^1$H NMR (CD$_3$OD) δ 1.07 (t, 3H, J=6.9 Hz), 1.22 (t, 3H, J=6.9 Hz), 2.04 (s, 3H), 3.11-3.45 (m, 5H), 3.65 (m, 1H), 4.98 (m, 2H), 5.82 (m, 1H), 6.28 (s, 1H); $^{13}$C NMR (CD$_3$OD) δ 11.3, 13.1, 14.1, 36.0, 40.2, 45.0, 101.6, 116.0, 116.3, 117.5, 137.1, 137.3, 153.1, 157.8, 172.3; IR ν$_{max}$ 3307, 1600, 1577, 1439, 1144 cm$^{-1}$; MS (ES) m/z: 264.10 ([MH]$^+$), 286.05 ([MNa]$^+$).

EXAMPLE 13

Preparation of Compound (vii)

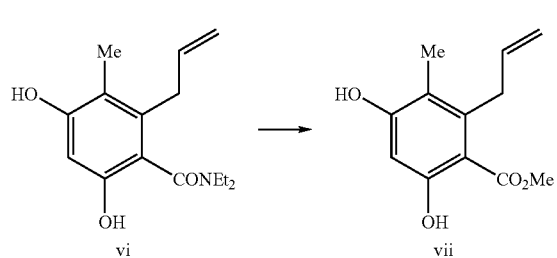

To a solution of vi (845 mg, 3.21 mmol) in CH$_2$Cl$_2$ (25 mL) was added Me$_3$OBF$_4$ (590 mg, 3.99 mmol) at room temperature. After 20 h, the reaction was concentrated and mixed with MeOH (9 mL) and saturated Na$_2$CO$_3$ solution (9 mL). After stirring at room temperature for 6 h, ether (50 mL) was added and the aqueous phase was adjusted to pH 2 using 0.5 N HCl. The crude was extracted with ether, and the combined ether extracts were washed with water and dried over MgSO$_4$. After concentration, the residue obtained was purified by FC (silica gel; Hexanes/EtOAc, 6:1) to give vii (520 mg, 73%) as white solid: $^1$H NMR (CDCl$_3$) δ 2.11 (s, 3H), 3.70 (dt, 2H, J=1.7, 5.8 Hz), 3.91 (s, 3H), 4.95 (m, 2H), 5.52 (s, 1H), 5.91 (m, 1H), 6.33 (s, 1H), 11.30 (s, 1H); $^{13}$C NMR (CDCl$_3$) δ 10.9, 35.6, 52.0, 101.5, 106.1, 114.9, 117.2, 136.2, 142.1, 159.2, 161.6, 171.9; IR ν$_{max}$ 3330, 1654, 1597, 1439, 1329, 1262, 1159 cm$^{-1}$; MS (ES) m/z: 286.05 ([MNa+MeCN]$^+$).

EXAMPLE 14

Preparation of Compound (viii)

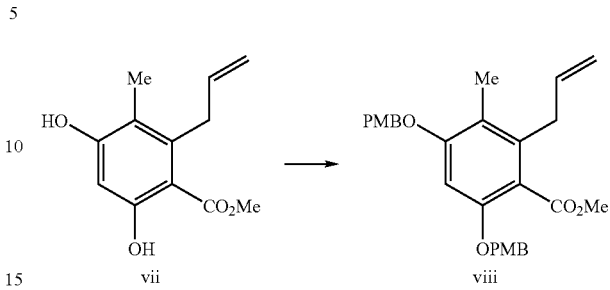

The mixture of compound vii (520 mg, 2.34 mmol), K$_2$CO$_3$ (971 mg, 7.03 mmol), PMBCl (953 uL, 7.02 mmol), Bu$_4$NI (173 mg, 0.47 mmol) and DMF (30 mL) was heated at 80° C. for 20 h. Remove DMF under vacuum (5 mmHg) at 50° C., add water and the crude was extracted with CH$_2$Cl$_2$. The combined organic extracts were washed with water, dried over MgSO$_4$ and concentrated. The residue obtained was purified by FC (silica gel; Hexanes/EtOAc, 9:1) to give viii (990 mg, 92%) as white solid: $^1$H NMR (CDCl$_3$) δ 2.12 (s, 3H), 3.35 (m, 2H), 3.78 (s, 3H), 3.80 (s, 3H), 3.82 (s, 3H), 4.93 (s, 2H), 4.97 (s, 2H), 4.99 (m, 2H), 5.85 (m, 1H), 6.46 (s, 1H), 6.91 (m, 4H), 7.27 (m, 4H); $^{13}$C NMR (CDCl$_3$) δ 11.0, 35.0, 51.9, 55.15, 55.18, 70.1, 70.6, 97.1, 113.8, 113.9, 115.6, 117.7, 118.6, 128.6, 128.8, 128.8, 128.9, 135.4, 136.9, 154.4, 158.1, 159.2, 159.3, 169.2; IR ν$_{max}$ 2949, 1725, 1593, 1515, 1250, 1155 cm$^{-1}$; MS (ES) m/z: 485.10 ([MNa]$^+$).

EXAMPLE 15

Preparation of Compound (6)

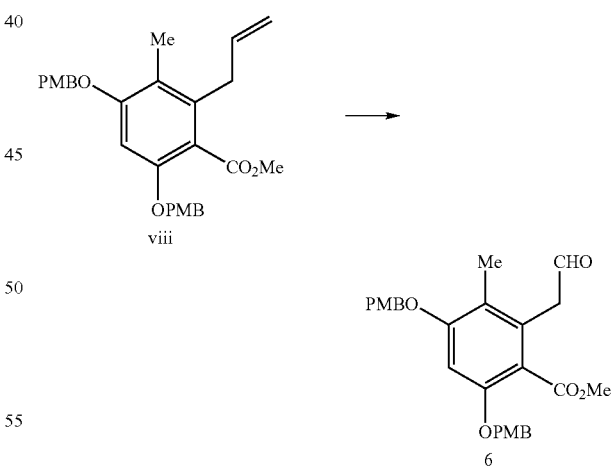

To a solution of viii (462 mg, 1 mmol) in THF (5 mL) and H$_2$O (1 mL) were added 4-methyl-morpholine-N-oxide (234 mg, 2 mmol) and OsO$_4$ (0.1 M solution in t-BuOH, 800 μL, 0.08 mmol) at 0° C. After stirring at ambient temperature for 12 h, 10% Na$_2$S$_2$O$_3$ solution was added. After 30 min, the crude was extracted with EtOAc and the combined organic extracts were washed with water and dried over MgSO$_4$. After concentration, the residue obtained was filtered through a short column (silica gel) and washed with EtOAc. Removal of the solvent from the combined filtrate gave the crude diol. NaIO$_4$ (321 mg, 1.5 mmol) was added to a solution of crude diol in 90% MeOH (25 mL). After stirring at room temperature for 1 h, EtOAc (50 mL) was added and the reaction mixture was washed with water and dried over MgSO$_4$. After concentration, the residue obtained was purified by FC (silica gel; CH$_2$Cl$_2$/EtOAc, 20:1) to give compound 6 (408 mg, 88%) as white crystals: $^1$H NMR (CDCl$_3$) δ 2.08 (s, 3H), 3.68 (d, 2H, J=1.8 Hz), 3.81 (s, 3H), 3.82 (s, 3H), 3.83 (s, 3H), 4.97 (s, 2H), 5.01 (s, 2H), 6.53 (s, 1H), 6.91 (m, 4H), 7.30 (m, 4H), 9.64 (t, 1H, J=1.8 Hz); $^{13}$C NMR (CDCl$_3$) δ 11.6, 45.8, 52.1, 55.2, 55.2, 70.1, 70.8, 98.2, 113.9, 114.0, 117.6, 119.5, 128.5, 128.6, 128.7, 128.8, 130.7, 155.3, 158.6, 159.3, 159.4, 168.6, 198.6; IR ν$_{max}$ 3000, 2951, 1722, 1594, 1515, 1250, 1156 cm$^{-1}$; MS (ES) m/z: 487.10 ([MNa]$^+$).

EXAMPLE 16

Preparation of Compound (16)

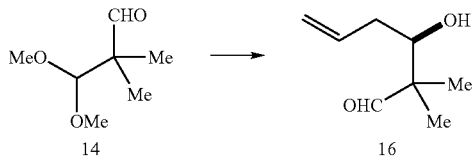

To a solution of 14 (Johnson, P. R.; White, J. D. J. Org. Chem. 1984, 49, 4424) (2.0 g, 14.1 mmol) in toluene (20 mL) was added allylsilane 15 (5.69 g, 21.1 mmol) at −15° C. After 48 h at −10° C., 0.5 N HCl (20 mL) was added to the reaction mixture and stirred at room temperature for 30 min. The crude was extracted with ether and combined organic extracts were washed with water, sat. NaHCO$_3$, brine and dried over MgSO$_4$. After concentration, the residue was purified by FC (silica gel; hexanes/EtOAc, 15:1) to give 16 (1.38 g, 69%, 94% ee) as a colorless oil: [α]$^{23}$$_D$=+3.73 (CH$_2$Cl$_2$, c=2.0); $^1$H NMR (CDCl$_3$) δ 1.08 (s, 3H), 1.11 (s, 3H), 2.07 (m, 1H), 2.15 (d, 1H, J=3.6 Hz), 2.32 (m, 1H), 3.78 (dt, 1H, J=3.6, 10.4 Hz), 5.17 (m, 2H), 5.85 (m, 1H), 9.57 (s, 1H); $^{13}$C NMR (CDCl$_3$) δ 16.5, 19.0, 36.2, 50.0, 73.8, 118.6, 134.9, 206.2; IR ν$_{max}$ 3417, 3077, 2977, 1724, 1642 cm$^{-1}$. MS (ES) m/z: 307.10 ([M$_2$Na]$^+$). The enantiomeric excess was determined from the H NMR spectrum of the Mosher ester derivative prepared with (S)-(−)-MTPA: major isomer has Me-resonances at 1.064 and 1.067 ppm; the minor isomer has Me-resonances at 1.094 and 1.100 ppm. Integration of the Me-resonances was used to calculate an ee of 94%.

EXAMPLE 17

Preparation of Compound (17)

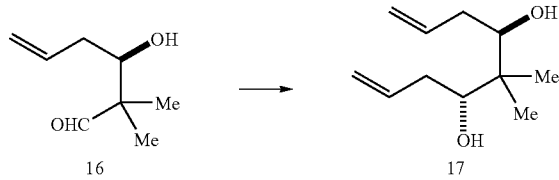

To a solution of 16 (1.30 g, 9.15 mmol) in toluene (15 mL) was added allylsilane 15 (4.93 g, 18.3 mmol) at −15° C. After kept at this temperature for 20 h, 0.5 N HCl (15 mL) was added to the reaction mixture and stirred at room temperature for 15 min. The crude was extracted with ether and the combined organic extracts were washed with water, sat. NaHCO$_3$, brine and dried over MgSO$_4$. After concentration, the residue was purified by FC (silica gel; hexanes/EtOAc, 15:1) to give 17 (1.33 g, 79%, dr=17:1) as white solid. [α]$^{22}$$_D$=+21.4 (CHCl$_3$, c=1.43); $^1$H NMR (CDCl$_3$) δ 0.94 (s, 6H), 2.11 (m, 2H), 2.32 (m, 2H), 3.13 (dm, 2H, J=3.4 Hz), 3.57 (ddd, 2H, J=2.9, 3.7, 10.7 Hz), 5.16 (m, 4H), 5.90 (m, 2H); $^{13}$C NMR (CDCl$_3$) δ 20.9, 36.4, 40.0, 77.4, 117.6, 136.2; IR ν$_{max}$ 3350, 3077, 2974, 1641, 1471, 1431 cm$^{-1}$; MS (ES) m/z: 207.05 ([MNa]$^+$). The $^{13}$C NMR data matches the reported data for racemic 17 (Trieselmann, T.; Hoffmann, R. W.; Menzel, K. Eur. J. Org. Chem. 2002, 1292).

EXAMPLE 18

Preparation of Compound (18)

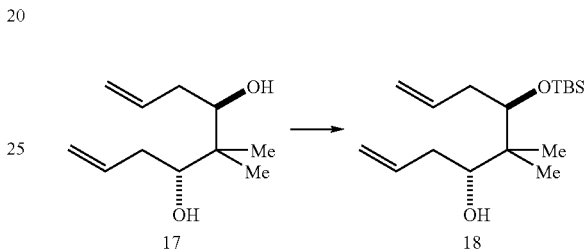

To a solution of 17 (465 mg, 2.53 mmol) and 2,6-lutidine (0.44 mL, 3.80 mmol) in CH$_2$Cl$_2$ (20 mL) was added TBSOTf (0.64 mL, 2.78 mmol) at 0° C. After stirring for 10 min, MeOH (1 mL) was added and stirred for 10 min. The solvent was removed under vacuo and the residue obtained was purified by FC (silica gel; hexanes/EtOAc, 50:1) to give 18 (692 mg, 92%) as a colorless oil: [α]$^{23}$$_D$=+29.2 (EtOAc, c=1.05); $^1$H NMR (CDCl$_3$) δ 0.09 (s, 3H), 0.10 (s, 3H), 0.80 (s, 3H), 0.90 (s, 9H), 1.00 (s, 3H), 2.13 (m, 2H), 2.33 (m, 1H), 2.52 (m, 1H), 3.57 (dd, 1H, J=4.6, 6.4 Hz), 3.87 (dd, 1H, J=4.1, 8.7 Hz), 5.10 (m, 4H), 5.91 (m, 2H); $^{13}$C NMR (CDCl$_3$) δ −4.2, −3.8, 18.1, 20.4, 23.3, 26.0, 36.4, 37.7, 41.2, 75.0, 83.2, 116.3, 116.8, 136.5, 136.8; IR ν$_{max}$ 3494, 3077, 2955, 1641, 1470, 1255 cm$^{-1}$; MS (ES) m/z: 299.15 ([MH]$^+$), 321.15 ([MNa]$^+$).

EXAMPLE 19

Preparation of Compound (19)

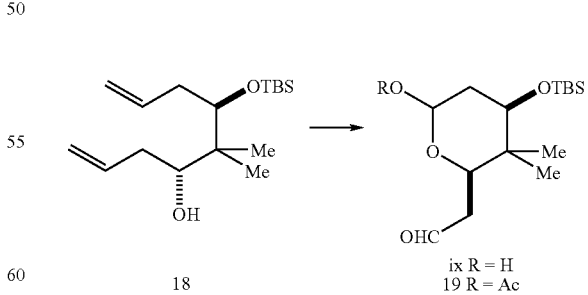

Ozone was bubbled through a solution of 18 (692 mg, 2.32 mmol) in CH$_2$Cl$_2$ (50 mL) at −78° C. until the solution became slightly blue. Ph$_3$P (2.43 g, 9.28 mmol) was added and the resultant solution was stirred at room temperature overnight. After concentration, the residue obtained was purified by FC (silica gel; hexanes/EtOAc, 10:1 to 3:1) to give hemiacetal ix (692 mg, 99%) as viscous oil. To a solution of ix in CH$_2$Cl$_2$ (18 mL) was added Et$_3$N (1.27 mL, 9.19 mmol), DMAP (50 mg) and Ac$_2$O (431 μL, 4.59 mmol) successively at 0° C. After 10 min, sat NaHCO$_3$ (20 mL) was added and the crude was extracted with ether. The combined ether extracts were washed with water, dried over MgSO$_4$ and concentrated. The residue obtained was purified by column chromatography (silica gel; hexanes/EtOAc, 6:1) to give 19 (633 mg, 81%) as a mixture of two epimers and was used without further separation. The compound with axial OAc has $^1$H NMR (CDCl$_3$) δ 2.13 (s, 3H), 3.75 (dd, 1H, J=5.2, 11.3 Hz), 4.13 (dd, 1H, J=2.9, 10.1 Hz), 6.12 (dd, 1H, J=0.9, 3.7 Hz), 9.71 (t, 1H, J=1.5 Hz); The compound with equatorial OAc has $^1$H NMR (CDCl$_3$) δ 2.09 (s, 3H), 3.49 (dd, 1H, J=4.9, 11.6 Hz), 3.71 (dd, 1H, J=3.1, 9.8 Hz), 5.68 (dd, 1H, J=2.8, 10.1 Hz), 9.74 (t, 1H, J=2.1 Hz); IR $v_{max}$ 2929, 2856, 1727, 1367, 1235, 1076, 833 cm$^{-1}$; MS (ES) m/z: 399.15 ([MNa+MeOH]$^+$).

EXAMPLE 20

Preparation of Compound (xi)

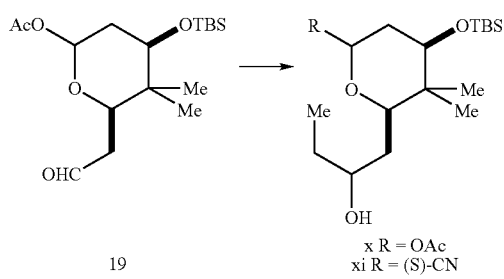

To a suspension of (R,R)-1,2-bis(trifluoromethanesulfonamido) cyclohexane in anhydrous toluene (10 mL) was added Ti(O$^i$Pr)$_4$ (2.16 mL, 7.32 mmol) at room temperature. After stirring at 45° C. for 40 min, the reaction was cooled to −78° C. and ZnEt$_2$ (1.0 M in hexanes, 7.32 mL, 7.32 mmol) was added dropwise. After 10 min, a solution of compound 19 (630 mg, 1.83 mmol) in toluene (10 mL) was added. After stirring for 8 h at −10° C., sat NH$_4$Cl (30 mL) was added and the reaction mixture was filtered through a pad of celite. The crude was extracted with EtOAc and the combined organic phases were washed with water and brine, dried over MgSO$_4$ and concentrated. The residue obtained was purified by column chromatography (silica gel; hexanes/EtOAc, 20:1) to give x (569 mg, 84%) as a mixture of four diastereomers and was used without further separation.

TMSCN (0.81 mL, 6.09 mmol) was added to x (569 mg, 1.53 mmol) and stirred at room temperature for 15 min. After cooled to 0° C., MeCN (20 mL), TMSCN (0.41 mL, 3.08 mmol) and ZnI$_2$ (114 mg, 0.36 mmol) were added successively and stirred for 40 min. Sat. NaHCO$_3$ solution (20 mL) was added and the reaction was extracted with EtOAc. The combined organic extracts were shaken with 1N HCl for 20 min and washed with aq. NaHCO$_3$ and water and dried over MgSO$_4$. After concentration, the residue obtained was purified by FC (silica gel; hexanes/EtOAc, 8:1) to give compound xi (471 mg, 91%) as a mixture of two alcohol epimers in the ratio of 3:1. The major isomer is a color less oil. [α]$^{24}_D$=+67.6 (EtOAc, c=0.55); $^1$H NMR (CDCl$_3$) δ 0.05 (s, 3H), 0.06 (s, 3H), 0.81 (s, 3H), 0.87 (s, 9H), 0.89 (s, 3H), 0.93 (t, 3H, J=7.4 Hz), 1.49 (m, 4H), 1.76 (ddd, 1H, J=1.2, 4.5, 13.8 Hz), 1.97 (ddd, 1H, J=6.0, 11.7, 13.8 Hz), 2.10 (s, 1H), 3.65 (m, 2H), 3.76 (dd, 1H, J=5.1, 6.6 Hz), 4.83 (dd, 1H, J=1.2, 6.0 Hz); $^{13}$C NMR (CDCl$_3$) δ −5.1, −4.3, 10.1, 12.3, 17.9, 22.5, 25.6, 30.4, 33.5, 35.4, 39.5, 63.7, 69.7, 72.3, 78.5, 117.8; IR $v_{max}$ 3436, 2959, 1472, 1258, 1104, 1082, 880 cm$^{-1}$; MS (ES) m/z: 364.20 ([MNa]$^+$). The minor is a colorless oil: [α]$^{25}_D$=+50.2 (EtOAc, c=0.69); $^1$H NMR (CDCl$_3$) δ 0.06 (s, 3H), 0.07 (s, 3H), 0.85 (s, 3H), 0.88 (s, 9H), 0.89 (s, 3H), 0.94 (t, 3H, J=7.4 Hz), 1.49 (m, 2H), 1.60 (dd, 1H, J=7.5, 10.2 Hz), 1.68 (ddd, 1H, J=2.7, 3.3, 11.4 Hz), 1.75 (ddd, 1H, J=1.2, 4.5, 13.5 Hz), 1.99 (ddd, 1H, J=6.0, 11.4, 13.5 Hz), 2.03 (s, 1H), 3.69 (m, 3H), 4.88 (dd, 1H, 1.2, 6.0 Hz); $^{13}$C NMR (CDCl$_3$) δ −5.02, −4.22, 9.66, 12.35, 17.90, 22.60, 25.66, 29.76, 33.41, 35.11, 39.88, 63.81, 71.99, 72.65, 82.85, 117.35; IR $v_{max}$ 3306, 2857, 1461, 1082, 884 cm$^{-1}$; MS (ES) m/z: 364.20 ([MNa]$^+$).

EXAMPLE 21

Preparation of Compound (xi)

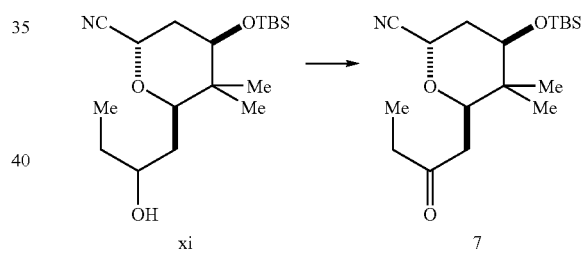

To a solution of xi (468 mg, 1.38 mmol) in CH$_2$Cl$_2$ (30 mL) was added Dess-Martin periodinane (2.0 g, 4.72 mmol) at 0° C. After stirring at ambient temperature for 3 h, 10% Na$_2$S$_2$O$_3$ solution (20 mL) was added and stirred for 10 min. The reaction was extracted with CH$_2$Cl$_2$ and the combined extracts were washed with NaHCO$_3$, water and dried over MgSO$_4$. After concentration, the residue obtained was purified by FC (silica gel; hexanes/EtOAc, 10:1) to give compound 7 (444 mg, 95%) as white solid: [α]$^{24}_D$=+40.6 (EtOAc, c=0.16); $^1$H NMR (CDCl3) δ 0.08 (s, 3H), 0.09 (s, 3H), 0.85 (s, 3H), 0.90 (s, 9H), 0.91 (s, 3H), 1.07 (t, 3H, J=7.3 Hz), 1.79 (ddd, 1H, J=1.5, 4.6, 13.7 Hz), 1.98 (ddd, 1H, J=6.1, 11.3, 13.7 Hz), 2.52 (m, 4H), 3.74 (dd, 1H, J=4.6, 11.3 Hz), 4.07 (dd, 1H, J=2.8, 9.8 Hz), 4.80 (dd, 1H, J=1.5, 6.1 Hz). $^{13}$C NMR (CDCl3) δ −5.0, −4.2, 7.5, 12.5, 17.9, 22.7, 25.7, 33.6, 36.1, 39.4, 42.4, 63.7, 72.1, 77.8, 117.2, 208.4; IR $v_{max}$ 3402, 2958, 1716, 1462, 1256, 1099, 885 cm$^{-1}$.

EXAMPLE 22

Preparation of Compound (20)

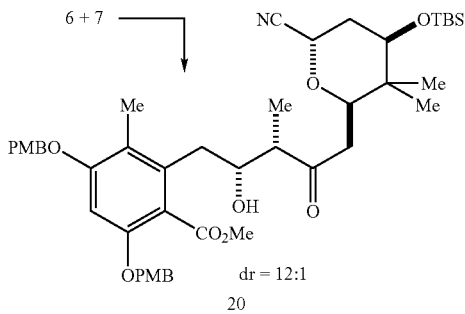

To a solution of compound 7 (100 mg, 0.296 mmol) in $CH_2Cl_2$ (3 mL) was added $PhBCl_2$ (46 μL, 0.35 mmol) at −78° C. After 20 min, DIPEA (75 uL, 0.43 mmol) was added. The reaction was stirred at −78° C. for 1 h and 0° C. for 1 h. Aldehyde 6 (165 mg, 0.35 mmol) in $CH_2Cl_2$ (1.5 mL) was added at −78° C. and the reaction was kept at this temperature for 3.5 h. A mixture of MeOH (4 mL) and pH 7 buffer (4 mL) was added −78° C. and the pH was adjusted to neutral using pH 8 buffer. After stirring at 0° C. for 1.5 h, the reaction was extracted with $CH_2Cl_2$ and the combined organic phases were washed with water and dried over $MgSO_4$. After concentration, the residue was purified by FC (silica gel; $CH_2Cl_2$/EtOAc, 20:1) to give compound 20 (210 mg, 88%, dr=12:1) as a white foam: $[\alpha]^{24}_D$=+42.3 (EtOAc, c=0.40); $^1H$ NMR ($CDCl_3$) δ 0.07 (s, 3H), 0.09 (s, 3H), 0.86 (s, 3H), 0.90 (s, 9H), 0.92 (s, 3H), 1.21 (d, 3H, J=7.0 Hz), 1.77 (ddd, 1H, J=1.3, 4.6, 13.6 Hz), 1.96 (ddd, 1H, J=6.0, 11.5, 13.6 Hz), 2.17 (s, 3H), 2.57 (m, 2H), 2.73 (m, 2H), 2.88 (dd, 1H, J=3.3, 14.3 Hz), 3.75 (m, 2H), 3.80 (s, 3H), 3.82 (s, 3H), 3.85 (s, 3H), 4.02 (m, 1H), 4.13 (dd, 1H, J=2.1, 9.0 Hz), 4.77 (d, 1H, 5.1 Hz), 4.95 (s, 4H), 6.47 (s, 3H), 6.89 (m, 4H), 7.28 (m, 4H); $^{13}C$ NMR ($CDCl_3$) δ −5.1, −4.3, 11.4, 11.6, 12.6, 17.8, 22.6, 25.6, 33.6, 35.2, 39.2, 42.0, 52.5, 52.7, 55.1, 55.1, 63.6, 70.0, 70.7, 71.4, 72.1, 77.3, 97.2, 113.7, 113.9, 117.2, 117.3, 118.7, 128.55, 128.64, 128.7, 136.6, 155.0, 158.8, 159.2, 159.3, 170.8, 210.5; IR $\nu_{max}$ 3430, 2954, 1715, 1593, 1515, 1250, 1159, 1082 $cm^{-1}$; MS (ES) m/z: 826.35 ([MNa]$^+$).

EXAMPLE 22

Preparation of Compound (21)

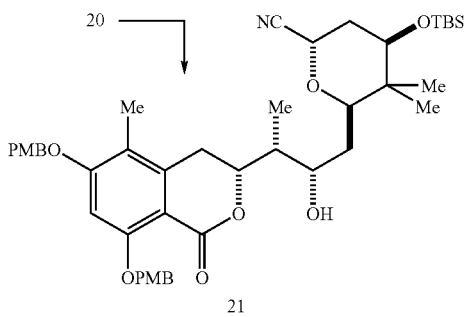

To a solution of 20 (100 mg, 125 μmol) in anhydrous THF (10 mL) was added catecholborane (1.0 M in THF, 3.74 mL, 3.74 mmol) at −78° C. After stirring at 0° C. for 20 h, 2 N NaOH (12 mL) was added and the resultant reaction mixture was stirred at ambient temperature for 0.5 h. The reaction was extracted by $CH_2Cl_2$ and the combined organic extracts were washed with 1 N NaOH solution until the aqueous phase is colorless and then washed with water. The extracts were dried over $MgSO_4$ and concentrated to give a white solid in quantitative yield, which is a 8:1 mixture of compound 21 and its diastereomer. Pure compound 21 was obtained through recrystallization from $CH_2Cl_2$/acetone. $[\alpha]^{22}_D$=−39.4 ($CH_2Cl_2$, c=0.20); $^1H$ NMR ($CDCl_3$) δ 0.08 (s, 3H), 0.10 (s, 3H), 0.88 (s, 3H), 0.90 (s, 9H), 0.93 (s, 3H), 1.12 (d, 3H, J=7.2 Hz), 1.74 (t, 2H, J=6.0 Hz), 1.79 (dd, 1H, J=4.6, 13.7 Hz), 1.91 (m, 1H), 2.01 (ddd, 1H, J=6.2, 11.9, 13.7 Hz), 2.10 (s, 3H), 2.83 (dd, 1H, J=12.0, 16.3 Hz), 2.96 (dd, 1H, J=2.6, 16.3 Hz), 3.68 (m, 2H), 3.80 (s, 3H), 3.82 (s, 3H), 4.07 (m, 1H), 4.41 (ddd, 1H, J=2.7, 4.9, 12.0 Hz), 4.87 (d, 1H, J=5.3 Hz), 4.98 (s, 2H), 5.09 (d, 1H, J=12.0 Hz), 5.16 (d, 1H, J=12.0 Hz), 6.49 (s, 1H), 6.90 (m, 4H), 7.30 (d, 2H, J=8.6 Hz), 7.44 (d, 2H, J=8.6 Hz); $^{13}C$ NMR ($CDCl_3$) δ −5.0, −4.2, 8.8, 11.1, 12.4, 17.9, 22.7, 25.7, 29.6, 32.9, 33.4, 40.0, 41.5, 55.2, 55.3, 63.8, 69.9, 70.9, 71.97, 72.0, 78.7, 83.0, 98.2, 107.5, 113.9, 114.0, 116.0, 117.4, 128.3, 128.5, 128.8, 141.4, 159.2, 159.5, 160.2, 161.0, 163.1; IR $\nu_{max}$ 3364, 1671, 1588, 1515, 1249, 1098 $cm^{-1}$; MS (ES) m/z: 796.50 ([MNa]$^+$), 812.45 ([MK]$^+$).

EXAMPLE 23

Preparation of Compound (xii)

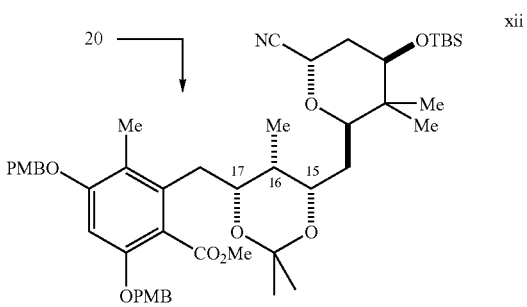

The acetonide-derivative xii of the diol obtained from 20 by omitting a basic workup (Na,K-tartrate workup instead), was prepared for determination of the relative stereochemistry. $^{13}C$ NMR (CDCl3) resonances of the acetonide Me peaks and quaternary carbon (19.5, 29.8, and 98.9 ppm) confirm the $C_{15}$,$C_{17}$-syn configuration (Rychnovsky, S. D.; Rogers, B.; Yang, G. J. Org. Chem. 1993, 58, 3511); the $^1H$ NMR $H_{16}$-$H_{17}$ coupling constant of 2.4 Hz (δ 4.02 ppm) is in agreement with an equatorial disposition of $H_{16}$, confirming the $C_{16}$,$C_{17}$-anti configuration. $^1H$ NMR ($CD_3OD$) δ 0.11 (s, 3H), 0.12 (s, 3H), 0.87 (s, 3H), 0.92 (s, 9H), 0.95 (d, 3H, J=6.4 Hz), 0.96 (s, 3H), 1.22 (s, 3H), 1.29 (s, 3H), 1.58 (m, 1H), 1.62 (m, 1H), 1.67 (m, 1H), 1.80 (ddd, 1H, J=1.2, 4.4, 14.0 Hz), 2.00 (ddd, 1H, J=5.6, 11.6, 14.0 Hz), 2.14 (s, 3H), 2.54 (dd, 1H, J=2.4, 14.4 Hz), 3.01 (dd, 1H, J=8.8, 14.4 Hz), 3.44 (dd, 1H, J=2.0, 11.8 Hz), 3.69 (dd, 1H, J=8.4, 11.6 Hz), 3.79 (s, 3H), 3.80 (s, 3H), 3.82 (s, 3H), 4.02 (ddd, 1H, J=2.4, 2.4, 8.8 Hz), 4.07 (ddd, 1H, J=1.6, 4.8, 13.2 Hz), 4.99 (bs, 4H), 6.60 (s, 1H), 6.90 (m, 4H), 7.30 (m, 4H); $^{13}C$ NMR ($CDCl_3$) δ −5.0, −4.2, 4.8, 11.8, 12.3, 17.9, 19.5, 22.6, 25.7, 29.8, 31.2, 33.5, 33.8, 34.2, 39.8, 52.1, 55.2, 55.3, 63.7, 70.1, 70.6, 70.8, 72.4, 74.8, 77.8, 97.3, 98.9, 113.8, 113.9, 117.6, 118.2, 119.6, 128.6, 128.8, 129.0, 129.1, 137.8, 154.3, 158.0, 159.2, 159.3, 169.3; MS (ES) m/z: 868.45 ([MNa]$^+$).

EXAMPLE 24

Preparation of Compound (22)

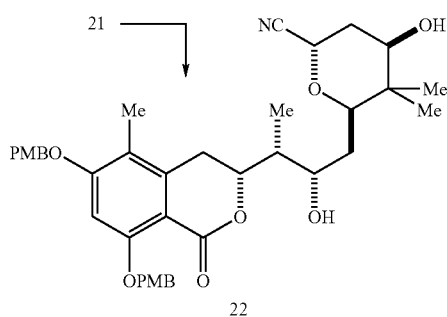

To a solution of 21 (50 mg, 65 μmol) in THF (10 mL) was added TBAF (1.0 M in THF, 100 μL, 0.1 mmol) at room temperature. After 2 h, the reaction was concentrated and the residue was purified by FC (silica gel; hexanes/EtOAc, 1:2 to EtOAc) to give 22 43 mg (quant.) as a viscous oil. $[\alpha]^{26}_D$=+ 33.6 (EtOAc, c=0.60); $^1$H NMR (CDCl$_3$) δ 0.91 (s, 3H), 1.02 (s, 3H), 1.11 (d, 3H, J=6.8 Hz), 1.76 (m, 2H), 1.89-2.06 (m, 3H), 2.10 (s, 3H), 2.84 (dd, 1H, J=12.0, 16.0 Hz), 2.94 (dd, 1H, J=2.8, 16.0 Hz), 3.68 (dd, 1H, J=4.6, 7.8 Hz), 3.76 (dd, 1H, J=4.8, 11.6 Hz), 3.80 (s, 3H), 3.83 (s, 3H), 4.07 (m, 1H), 4.43 (ddd, 1H, J=2.8, 4.4, 11.6 Hz), 4.91 (d, 1H, J=4.8 Hz), 4.98 (s, 2H), 5.10 (d, 1H, J=12.2 Hz), 5.16 (d, 1H, J=12.2 Hz), 6.49 (s, 1H), 6.90 (t, 4H, J=8.4 Hz), 7.29 (d, 2H, J=8.4 Hz), 7.43 (d, 2H, J=8.4 Hz); $^{13}$C NMR (CDCl$_3$) δ 8.8, 11.1, 12.1, 22.2, 29.6, 32.5, 32.6, 39.5, 41.4, 55.2, 55.3, 64.0, 69.9, 70.9, 71.5, 72.0, 78.6, 82.7, 98.1, 107.4, 113.9, 114.0, 116.0, 117.2, 128.2, 128.5, 128.7, 128.8, 141.4, 159.2, 159.5, 160.2, 161.1, 163.2; IR ν$_{max}$ 3394, 2966, 1674, 1588, 1514, 1248, 1097 cm$^{-1}$; MS (ES) m/z: 682.35 ([MNa]$^+$).

EXAMPLE 25

Preparation of Compound (22a)

A. Synthesis

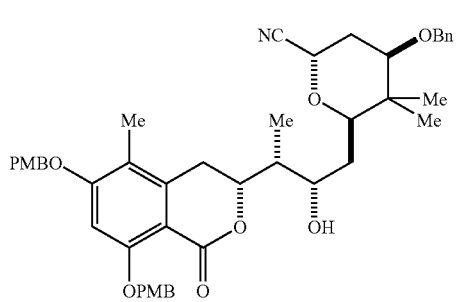

M. p. (acetone) 197° C.; $^1$H NMR (CDCl$_3$) δ 0.95 (s, 3H), 1.00 (s, 3H), 1.11 (d, 3H, J=7.2 Hz), 1.74 (m, 2H), 1.89 (m, 1H), 1.97 (m, 1H), 2.04 (m, 1H), 2.10 (s, 3H), 2.83 (s, 1H), 2.84 (dd, 1H, J=12.0, 16.0 Hz), 2.95 (dd, 1H, J=2.8, 16.0 Hz), 3.44 (dd, 1H, J=4.6, 11.4 Hz), 3.68 (dd, 1H, J=6.8, 6.8 Hz), 3.80 (s, 3H), 3.83 (s, 3H), 4.06 (m, 1H), 4.42 (ddd, 1H, J=2.8, 4.8, 12.0 Hz), 4.50 (d, 1H, J=11.6 Hz), 4.63 (d, 1H, J=11.6 Hz), 4.93 (d, 1H, J=4.8 Hz), 4.98 (s, 2H), 5.10 (d, 1H, J=12.0 Hz), 5.16 (d, 1H, J=12.0 Hz), 6.49 (s, 1H), 6.90 (m, 4H), 7.28~7.45 (m, 9H); $^{13}$C NMR (CDCl$_3$) δ 8.9, 11.1, 13.1, 22.4, 29.6, 32.6, 39.5, 41.5, 55.2, 55.3, 64.0, 69.9, 70.9, 71.9, 72.0, 78.6, 78.7, 83.3, 98.2, 107.5, 113.9, 114.0, 116.0, 117.2, 127.6, 127.8, 128.3, 128.4, 128.5, 128.7, 128.8, 138.0, 141.4, 159.2, 159.5, 160.2, 161.0, 163.1; IR ν$_{max}$ 3369, 2963, 1669, 1513, 1247, 1097 cm$^{-1}$; MS (ES) m/z: 772.25, ([MNa]$^+$).

B. Crystallographic Analysis

Crystals of 22a for single crystal X-ray analysis were obtained by the slow evaporation from acetone (colorless needles, m.p.:197° C.). X-ray data were collected using a Bruker Kappa CCD (charge couple device) based diffractometer. A suitable crystal (0.2 mm×0.2 mm×0.8 mm) was mounted on a glass fiber. Data were measured using phi scans of 2° per frame for 60 seconds using "collect" data collection software, Nonius 1999. The data were processed using HKL2000 (Z. Otwinowski et al., "Processing of X-ray Diffraction Data Collected in Oscillation Mode", *Methods in Enzymology*, Volume 276: Macromolecular Crystallography, part A, p. 307-326, 1997, C. W. Carter, Jr. & R. M. Sweet, Eds., Academic Press (New York). Based on the systematic absences the crystals were monoclinc belonging to the space group P2$_1$. The structure was solved using SHELXS-90 (Sheldrick, G. M. SHELXS-90 Program for the solution of Crystal Structure, University of Gottingen, Germany, 1990) and refined by least-squares methods on F$^2$ using SHELXL-97 (Sheldrick, G. M. SHELXL-97 Program for the refinement of Crystal Structure, University of Gottingen, Germany, 1997). Non-hydrogen atoms were refined anisotropically and the hydrogen atoms located in the difference fourier densities were refined isotropically. The crystal was stable during data collection. FIG. 1 drawing depicts an ORTEP (Michael N. Burnett et al., ORTEP-III: Oak Ridge Thermal Ellipsoid Plot Program for Crystal Structure Illustrations, Oak Ridge National Laboratory Report ORNL-6895, 1996).

EXAMPLE 26

Preparation of Compound (23)

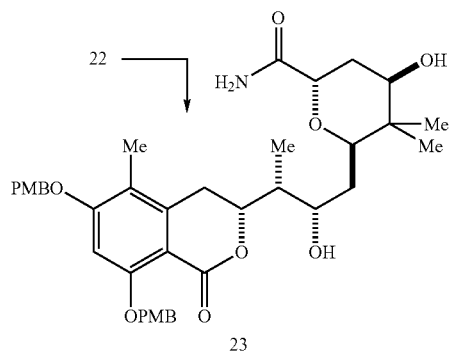

To a suspension of 22 (42 mg, 64 µmol) in 80% ethanol (8 mL) was added [PtH(PMe$_2$OH)(PMe$_2$O)$_2$H] (7 mg, 16 µmol). After refluxing in air for 80 min, the reaction was cooled to room temperature. Water was added and the crude was extracted with EtOAc. The combined organic extracts were washed with water, dried over MgSO$_4$ and concentrated to give a residue which was purified by FC (silica gel; CH$_2$Cl$_2$/MeOH 20:1) to give 23 (42 mg, 97%) as a viscous oil. [α]$^{27}_D$=+37.5 (EtOAc, c=0.43); $^1$H NMR (CDCl$_3$) δ 0.89 (s, 3H), 0.91 (s, 3H), 1.13 (d, 3H, J=7.2 Hz), 1.67 (m, 2H), 1.79 (m, 1H), 1.88 (m, 1H), 2.09 (s, 3H), 2.46 (dd, 1H, J=3.8, 13.0 Hz), 2.82 (dd, 1H, J=3.2, 16.4 Hz), 2.89 (dd, 1H, J=12.0, 16.4 Hz), 3.37 (d, 1H, J=8.0 Hz), 3.41 (dd, 1H, J=4.4, 11.6 Hz), 3.80 (s, 3H), 3.83 (s, 3H), 4.11 (bd, 1H, J=7.6 Hz), 4.42 (ddd, 1H, J=3.2, 3.6, 11.6 Hz), 4.45 (d, 1H, J=6.4 Hz), 4.99 (s, 2H), 5.08 (d, 1H, J=12.0 Hz), 5.16 (d, 1H, J=12.0 Hz), 5.59 (bs, 1H), 6.51 (s, 1H), 6.91 (t, 4H, J=8.0 Hz), 7.29 (d, 2H, J=8.8 Hz), 7.42 (d, 2H, J=8.8 Hz), 7.75 (bs, 1H); $^{13}$C NMR (CDCl$_3$) δ 7.9, 11.1, 11.9, 22.5, 29.2, 29.2, 34.2, 38.6, 41.7, 55.3, 55.3, 70.0, 70.9, 71.9, 73.8, 74.1, 80.0, 81.2, 98.0, 107.0, 114.0, 114.1, 115.9, 128.1, 128.5, 128.6, 128.9, 141.3, 159.3, 159.6, 160.5, 161.3, 162.7, 174.0; IR ν$_{max}$ 3402, 2965, 1682, 1596, 1515, 1247, 1157, 1081 cm$^{-1}$; MS (ES) m/z: 700.35 ([MNa]$^+$).

EXAMPLE 27

Preparation of Compound (24)

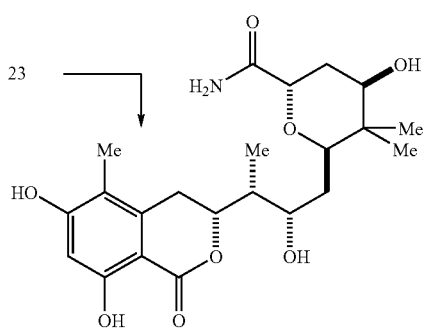

10% Pd/C (10 mg) was added to a solution of 23 (40 mg, 59 mmol) in ethanol (10 mL) and hydrogenated (H$_2$, 1 atm) for 24 h. The catalyst was filtered and ethanol was removed under reduced pressure. The residue obtained was purified by FC (silica gel; CH$_2$Cl$_2$/MeOH 10:1) to give 24 (26 mg) in quantitative yield as viscous oil. [α]$^{22}_D$=+34.0 (EtOAc, c=0.20); $^1$H NMR (CDCl$_3$/CD$_3$OD, 10/1) δ 0.85 (s, 3H), 0.88 (s, 3H), 1.09 (d, 3H, J=6.8 Hz), 1.67 (m, 2H), 1.78 (ddd, 1H, J=6.8, 12.0, 13.2 Hz), 1.88 (m, 1H), 2.01 (s, 3H), 2.30 (ddd, 1H, J=1.4, 4.6, 9.0 Hz), 2.88 (m, 2H), 3.30 (dd, 1H, J=4.4, 11.6 Hz), 3.34 (m, 1H), 4.01 (ddd, 1H, J=2.4, 7.8, 7.8 Hz), 4.39 (dd, 1H, J=6.0 Hz), 4.52 (ddd, 1H, J=4.4, 6.0, 10.0 Hz), 5.97 (bs, 1H), 6.25 (s, 1H), 7.78 (bs, 1H); $^{13}$C NMR δ 8.2, 10.3, 11.9, 22.4, 27.9, 28.9, 33.7, 38.4, 42.0, 71.3, 73.1, 73.3, 81.0, 81.1, 100.5, 114.1, 139.1, 161.8, 162.0, 162.9, 170.6, 175.1; IR ν$_{max}$ 3401, 2967, 1659, 1651, 1376, 1254 cm$^{-1}$; MS (ES) m/z: 460.20 ([MNa]$^+$).

EXAMPLE 28

Preparation of Compound (25)

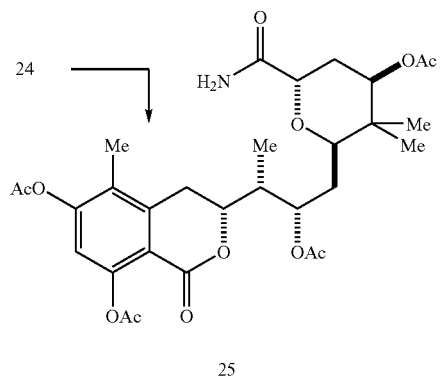

To a solution of 24 (25 mg, 57 µmol) was dissolved in pyridine (2.5 mL) was added Ac$_2$O (1.25 mL) at room temperature. After 20 h, EtOAc (20 mL) and sat. NaHCO$_3$ (10 mL) was added at 0° C. and stirred at room temperature for 15 min. The organic phase was separated, washed with water, 1N HCl and water, and dried over MgSO$_4$. After concentration, the residue obtained was purified by FC (silica gel; EtOAc/hexanes 2:1) to give compound 25 (32 mg, 92%) as a viscous oil. [α]$^{22}_D$=+48.4 (CH$_2$Cl$_2$, c=0.80); $^1$H NMR (CDCl$_3$) δ 0.94 (s, 3H), 0.95 (s, 3H), 1.17 (d, 3H, J=7.2 Hz), 1.79 (ddd, 1H, J=2.4, 4.8, 15.2 Hz), 1.91 (ddd, 1H, J=5.2, 9.2, 13.6 Hz), 2.06 (s, 3H), 2.08 (s, 3H), 2.10 (s, 3H), 2.12 (m, 1H), 2.26 (m, 2H), 2.33 (s, 3H), 2.35 (s, 3H), 2.78 (dd, 1H, J=12.0, 16.4 Hz), 3.04 (dd, 1H, J=2.8, 16.4 Hz), 3.46 (dd, 1H, J=2.4, 11.6 Hz), 4.38 (m, 2H), 4.83 (dd, 1H, J=4.0, 8.4 Hz), 5.29 (m, 1H), 5.48 (bs, 1H), 6.82 (bs, 1H), 6.84 (s, 1H); $^{13}$C NMR (CDCl$_3$) δ 9.4, 12.1, 14.2, 16.7, 20.8, 21.0, 21.1, 21.4, 24.2, 27.4, 28.7, 30.6, 37.0, 40.5, 72.2, 73.4, 78.3, 79.6, 115.7, 117.0, 125.7, 141.1, 150.5, 153.1, 161.5, 168.3, 169.5, 170.0, 171.0, 173.4; IR ν$_{max}$ 3466, 2975, 1771, 1727, 1693, 1598, 1371, 1241, 1192, 1060 cm$^{-1}$; MS (ES) m/z: 628.15 ([MNa]$^+$).

EXAMPLE 29

Preparation of Compounds (28-a) and (28-b)

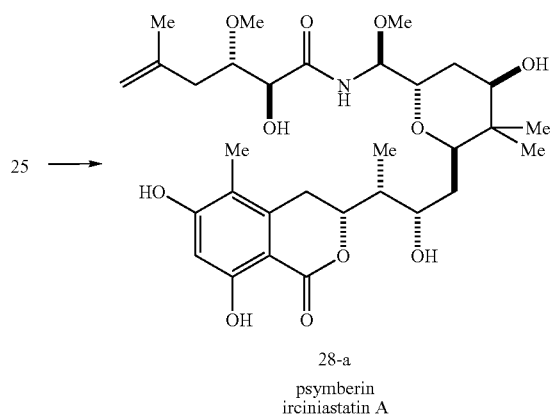

28-a
psymberin
irciniastatin A

-continued

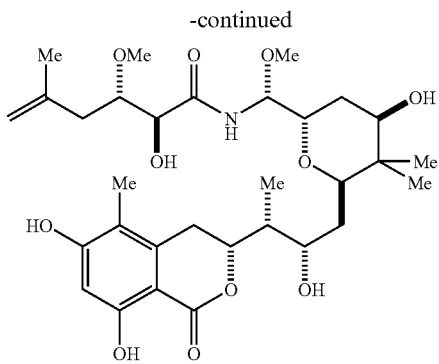

28-b

To a solution of acid anti-5 (43 mg, 155 μmol) in CH$_2$Cl$_2$ (2.5 mL) was added oxalyl chloride (54 μL, 620 μmol) and a catalytic amount of DMF at 0° C. After stirring at room temperature for 2 h, solvent was removed by N$_2$ flushing. The acid chloride obtained was dried on vacuum pump for 5 min and dissolved in CH$_2$Cl$_2$ (770 μL) to give a 0.2 M solution of compound anti-27.

To a mixture of compound 25 (14.5 mg, 24 μmol) and poly(2-vinylpyridine) (30 mg, 286 μmol) in CH$_2$Cl$_2$ (1.5 mL) was added Me$_3$OBF$_4$ (17.7 mg, 120 μmol) at room temperature. After 1.5 h, ether (3 mL) was added and allowed to stir for 5 min to precipitate the excess Me$_3$OBF$_4$. The reaction mixture was filtered and the solvent was removed by N$_2$ flushing. The residue obtained was dissolved in anhydrous toluene (2 mL) and cooled to 0° C. DIPEA (83 μL, 0.48 mmol) and anti-27 (0.2 M solution prepared in situ, 360 μL, 72 μmol) was added at 0° C. and the reaction mixture was stirred at 40° C. for 80 min. Anti-27 (0.2 M solution in CH$_2$Cl$_2$, 120 μL, 24 μmol) was added again and stirred for another 40 min and cooled to 0° C. NaBH$_4$ (45 mg) and ethanol (2 mL) was added and the reaction mixture was stirred at 0° C. for 2 h. EtOAc was added and the crude was washed with water and dried over MgSO$_4$. After concentration, the residue was roughly purified by FC (silica gel, EtOAc/hexanes, 1.5:1) to give a mixture of peracetylated compounds. This mixture was dissolved in MeOH (3 mL) and 1 N LiOH (0.6 mL) was added. After stirring at room temperature for 6 h, EtOAc was added and the aqueous phase was adjusted to pH 6 using 0.05 N NaHSO$_4$. The crude was extracted with EtOAc and the combined organic extracts were washed with sat. NaHCO$_3$, water and dried over MgSO$_4$. After concentration, the residue was purified by FC (silica gel, CH$_2$Cl$_2$/MeOH, 20:1) to give compound 28-a (5.8 mg) and 28-b (2.4 mg) in 56% total yield from 25 (ratio determined by H NMR of crude mixture: 71:29).

Figure 2:
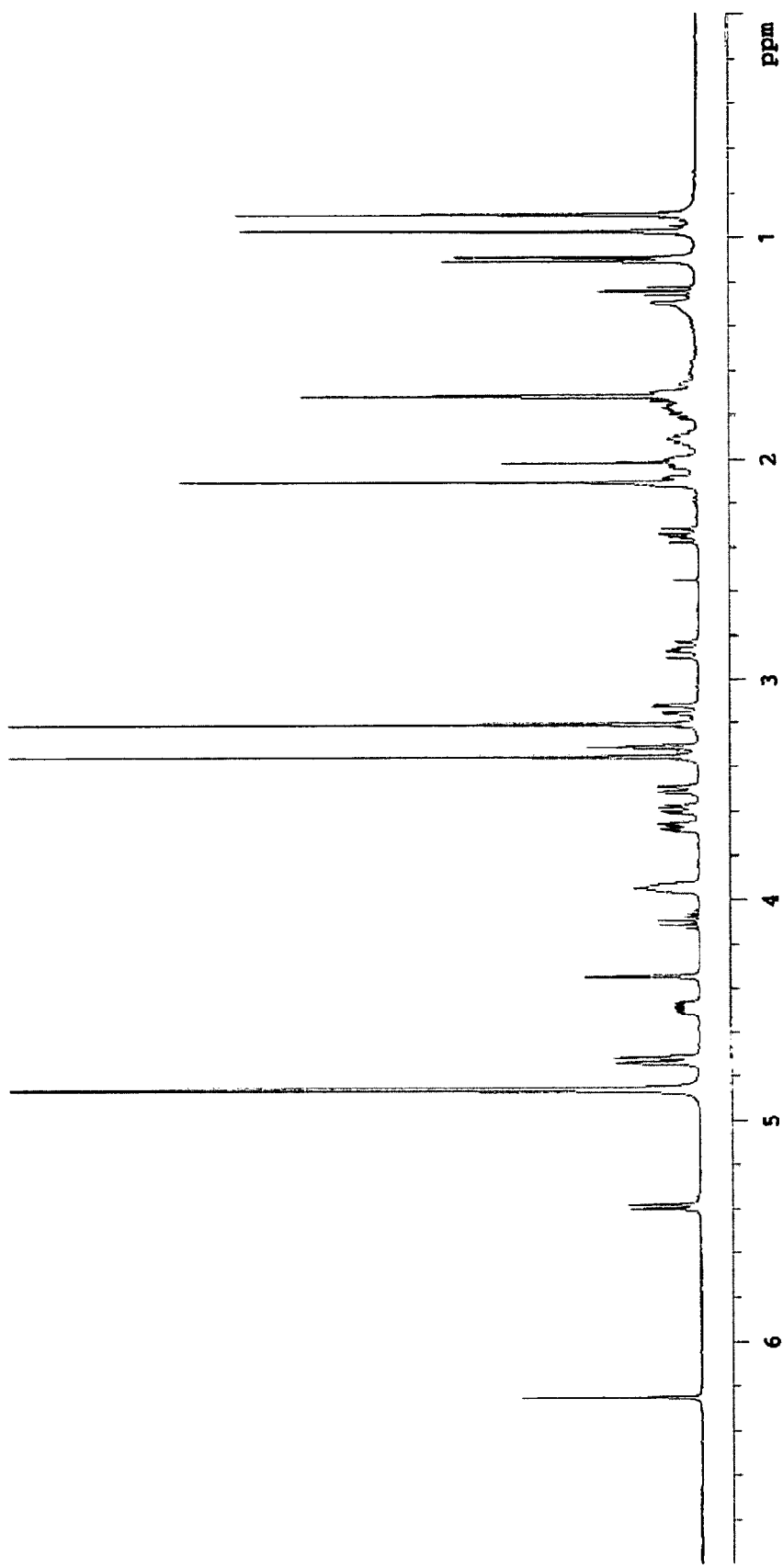
FIG. 2 is the $^1$H-NMR spectrum of compound 28-a in $CD_3OD$.
Figure 3:
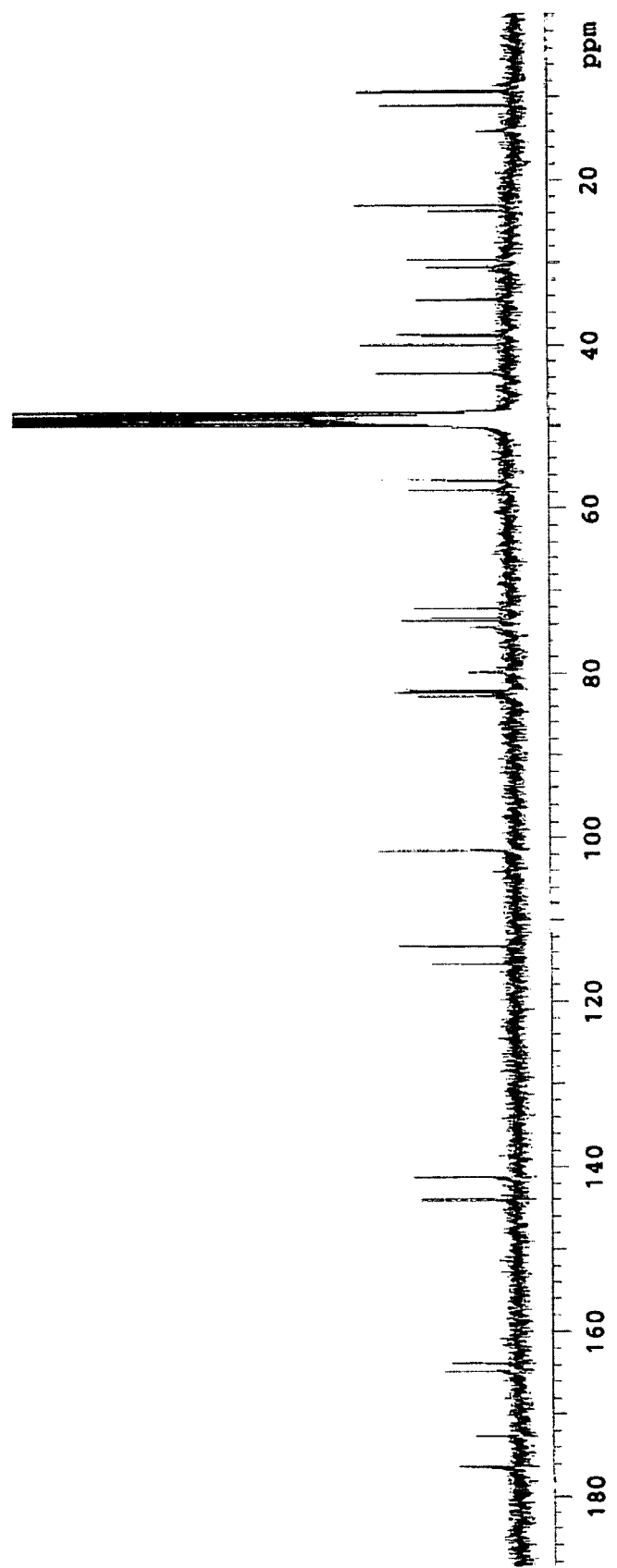
FIG. 3 is the $^{13}$C-NMR spectrum of compound 28-a in $CD_3OD$.

28-a: $[\alpha]^{23}_D$=+25.2 (MeOH, c=0.11); $^1$H NMR (CD$_3$OD; FIG. 2) δ 0.89 (s, 3H), 0.97 (s, 3H), 1.09 (d, 3H, J=6.8 Hz), 1.71 (s, 3H), 1.74 (m, 2H), 1.77 (ddd, 1H, J=6.4, 11.0, 13.2 Hz), 1.91 (ddq, 1H, J=2.4, 6.0, 6.8 Hz), 2.01 (ddd, 1H, J=2.8, 4.2, 13.2 Hz), 2.08 (dd, 1H, J=3.2, 14.4 Hz), 2.10 (s, 3H), 2.35 (dd, 1H, J=9.4, 14.4 Hz), 2.85 (dd, 1H, J=12.2, 16.6 Hz), 3.13 (dd, 1H, J=3.2, 16.6 Hz), 3.21 (s, 3H), 3.35 (s, 3H), 3.50 (dd, 1H, J=1.6, 11.2 Hz), 3.59 (dd, 1H, J=4.2, 11.0 Hz), 3.67 (ddd, 1H, J=2.8, 3.2, 9.4 Hz), 3.94 (m, 2H), 4.35 (d, 1H, J=2.4 Hz), 4.49 (ddd, 1H, J=3.2, 6.0, 12.2 Hz), 4.72 (bs, 1H), 4.74 (bs, 1H), 5.38 (d, 1H, J=8.0 Hz), 6.25 (s, 1H); $^1$H NMR (CDCl$_3$) δ 0.92 (s, 3H), 0.98 (s, 3H), 1.09 (d, 3H, J=7.2 Hz), 1.62 (m, 2H), 1.76 (s, 3H), 1.80 (m, 1H), 1.88 (m, 1H), 2.04 (s, 3H), 2.07 (m, 1H), 2.18 (dd, 1H, J=4.0, 14.6 Hz), 2.37 (dd, 1H, J=8.8, 14.6 Hz), 2.82 (dd, 1H, J=12.0, 16.8 Hz), 2.91 (dd, 1H, J=4.0, 16.8 Hz), 3.38 (s, 6H), 3.53 (d, 1H, J=10.0 Hz), 3.67 (dd, 1H, J=4.4, 11.8 Hz), 3.74 (ddd, 1H, J=3.2, 4.0, 8.8 Hz), 3.88 (ddd, 1H, J=2.4, 6.4, 8.0 Hz), 3.95 (dm, 1H, J=8.8 Hz), 4.40 (d, 1H, J=3.2 Hz), 4.54 (ddd, 1H, J=4.0, 4.8, 12.0 Hz), 4.80 (bs, 2H), 5.45 (dd, 1H, J=8.8, 10.0 Hz), 7.09 (d, 1H, J=10.0 Hz), 6.30 (s, 1H), 11.15 (bs, 1H); $^{13}$C NMR (CD$_3$OD; FIG. 3) δ 7.7, 9.4, 12.5, 21.5, 22.2, 28.1, 29.0, 32.9, 37.2, 38.4, 41.8, 55.1, 56.1, 70.6, 71.7, 72.0, 72.8, 78.4, 80.5, 80.8, 81.2, 99.9, 111.6, 113.8, 139.7, 142.2, 162.3, 163.1, 171.0, 174.9; $^{13}$C NMR (CDCl$_3$) δ 9.2, 10.4, 13.5, 22.7, 23.0, 28.4, 29.6, 32.1, 37.5, 38.7, 42.6, 56.2, 57.9, 71.4, 73.0, 73.9, 78.2, 79.5, 80.5, 81.9, 101.3, 101.4, 113.0, 113.3, 139.6, 142.0, 161.1, 162.3, 170.5, 173.6; IR v$_{max}$ 3368, 2932, 1660, 1652, 1622, 1506, 1456, 1378, 1253, 1174, 1108, 1069, 973, 896 cm$^{-1}$; MS (ES) m/z: 632.25 ([MNa]$^+$).

Figure 4:
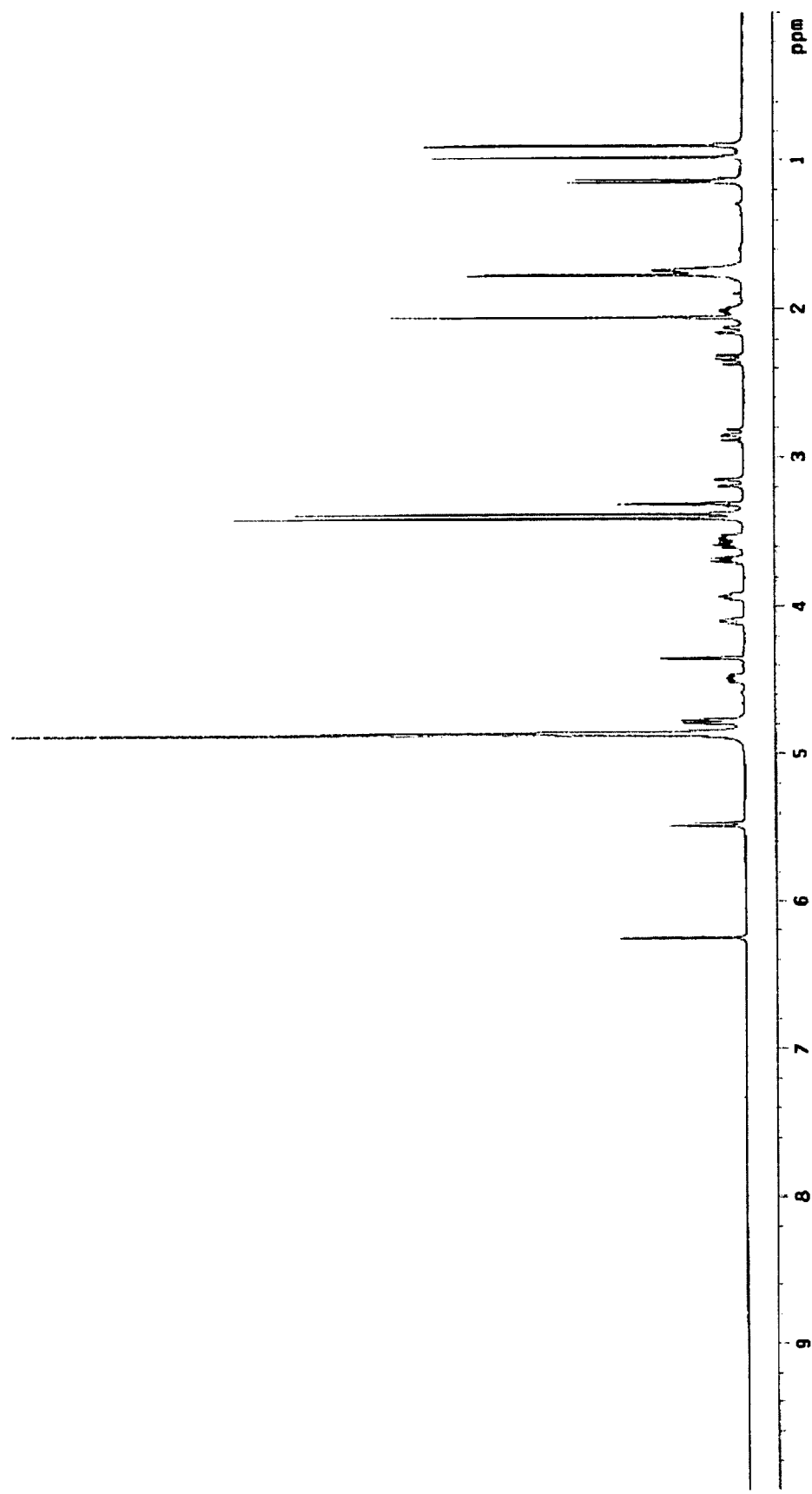
FIG. 4 is the $^1$H-NMR spectrum of compound 28-b in $CD_3OD$.
Figure 5:
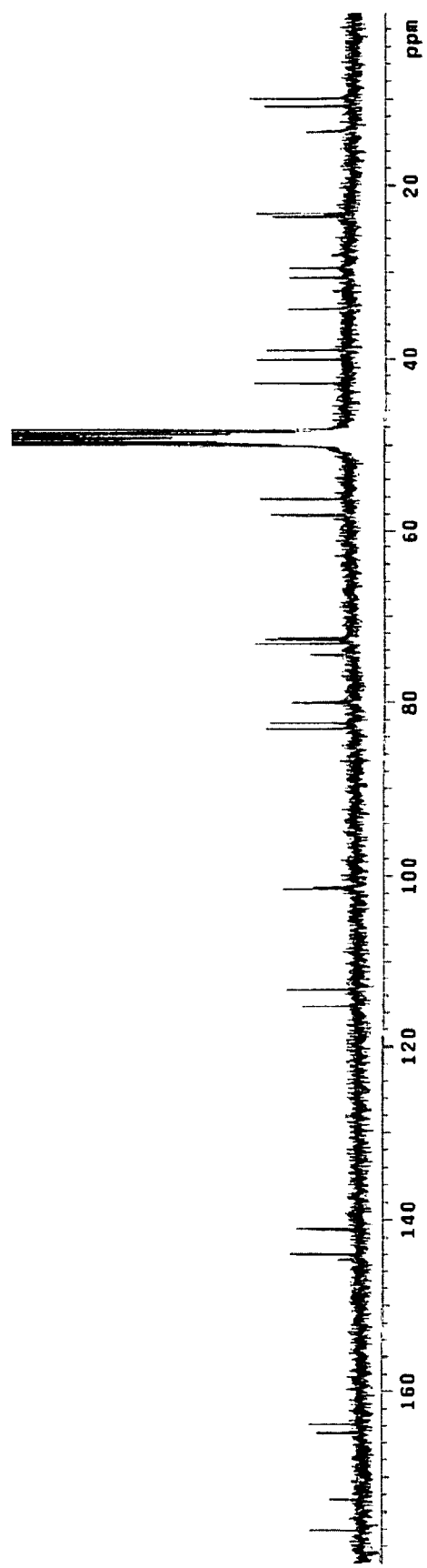
FIG. 5 is the $^{13}$C-NMR spectrum of compound 28-b in $CD_3OD$.

28-b: $[\alpha]_D$=−19.2 (MeOH, c=0.12); $^1$H NMR (CD$_3$OD; FIG. 4) δ 0 0.89 (s, 3H), 0.97 (s, 3H), 1.13 (d, 3H, J=6.8 Hz), 1.73 (m, 4H), 1.77 (s, 3H), 2.00 (m, 1H), 2.06 (s, 3H), 2.14 (dd, 1H, J=3.2, 14.6 Hz), 2.34 (dd, 1H, J=9.2, 14.6 Hz), 2.85 (dd, 1H, J=12.4, 16.8 Hz), 3.17 (dd, 1H, J=3.0, 16.8 Hz), 3.38 (s, 3H), 3.41 (s, 3H), 3.53 (dd, 1H, J=4.0, 8.0 Hz), 3.58 (dd, 1H, J=6.0, 10.0 Hz), 3.69 (ddd, 1H, J=3.2, 3.6, 9.2 Hz), 3.93 (m, 1H), 4.11 (m, 1H), 4.35 (d, 1H, J=3.2 Hz), 4.49 (ddd, 1H, J=3.0, 6.8, 12.4 Hz), 4.77 (bs, 1H), 4.79 (bs, 1H), 5.48 (d, 1H, J=8.8 Hz), 6.25 (s, 1H); $^1$H NMR (CDCl$_3$) δ 0.92 (s, 3H), 0.99 (s, 3H), 1.15 (d, 3H, J=7.2 Hz), 1.76 (s, 3H), 1.77 (m, 1H), 1.88 (m, 1H), 1.94 (m, 1H), 2.05 (s, 3H), 2.11 (dd, 1H, J=3.0, 14.4 Hz), 2.29 (dd, 1H, J=8.8, 14.4 Hz), 2.91 (dd, 1H, J=12.0, 16.4 Hz), 3.02 (dd, 1H, J=2.8, 16.4 Hz), 3.14 (bs, 1H), 3.41 (s, 3H), 3.42 (s, 3H), 3.63 (d, 1H, J=10.4 Hz), 3.73 (m, 2H), 3.90 (m, 1H), 4.07 (m, 2H), 4.41 (bs, 1H), 4.58 (ddd, 1H, J=3.0, 5.2, 12.0 Hz), 4.80 (bs, 1H), 4.83 (bs, 1H), 5.35 (dd, 1H, J=7.6, 9.6 Hz), 6.00 (bs, 1H), 6.30 (s, 1H), 7.17 (d, 1H, J=9.6 Hz), 11.2 (s, 1H); $^{13}$C NMR (CD$_3$OD; FIG. 5) δ 9.9, 10.8, 13.6, 23.2, 23.5, 29.5, 30.5, 34.2, 38.9, 40.1, 42.9, 56.2, 58.1, 72.5, 72.7, 73.2, 74.5, 79.9, 80.1, 82.5, 83.1, 101.4, 101.6, 113.4, 115.2, 141.2, 144.0, 163.8, 164.9, 172.6, 176.2; IR v$_{max}$ 3396, 2931, 1652, 1511, 1462, 1376, 1254, 1173, 1108, 1067 cm$^{-1}$; MS (ES) m/z: 632.25 ([MNa]$^+$).

EXAMPLE 30

Preparation of Compounds (29-a) and (29-b)

25 →

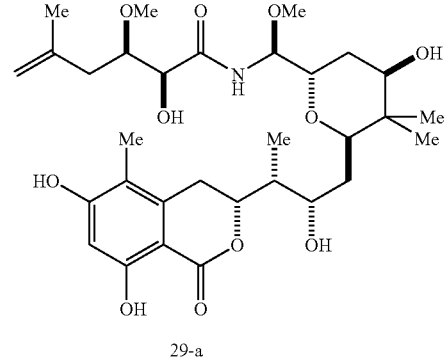

29-a

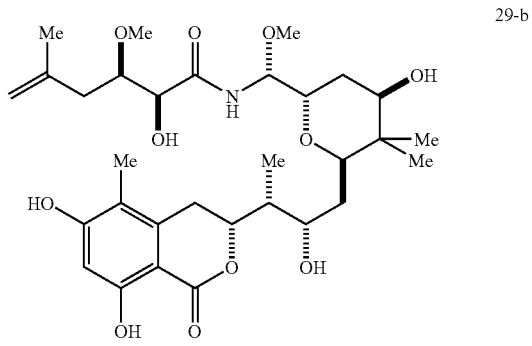

29-b

Compounds 29-a and 29-b were prepared (2.4 mg, 48% yield, 75:25 ratio) from compound 25 (5 mg, 8.2 μmol) and syn-27 using the same procedure described for the synthesis of 28-a and 28-b. They were inseparable, but partial separation could be achieved before acetate hydrolysis. 29-a could be obtained diastereomerically pure.

Figure 6:
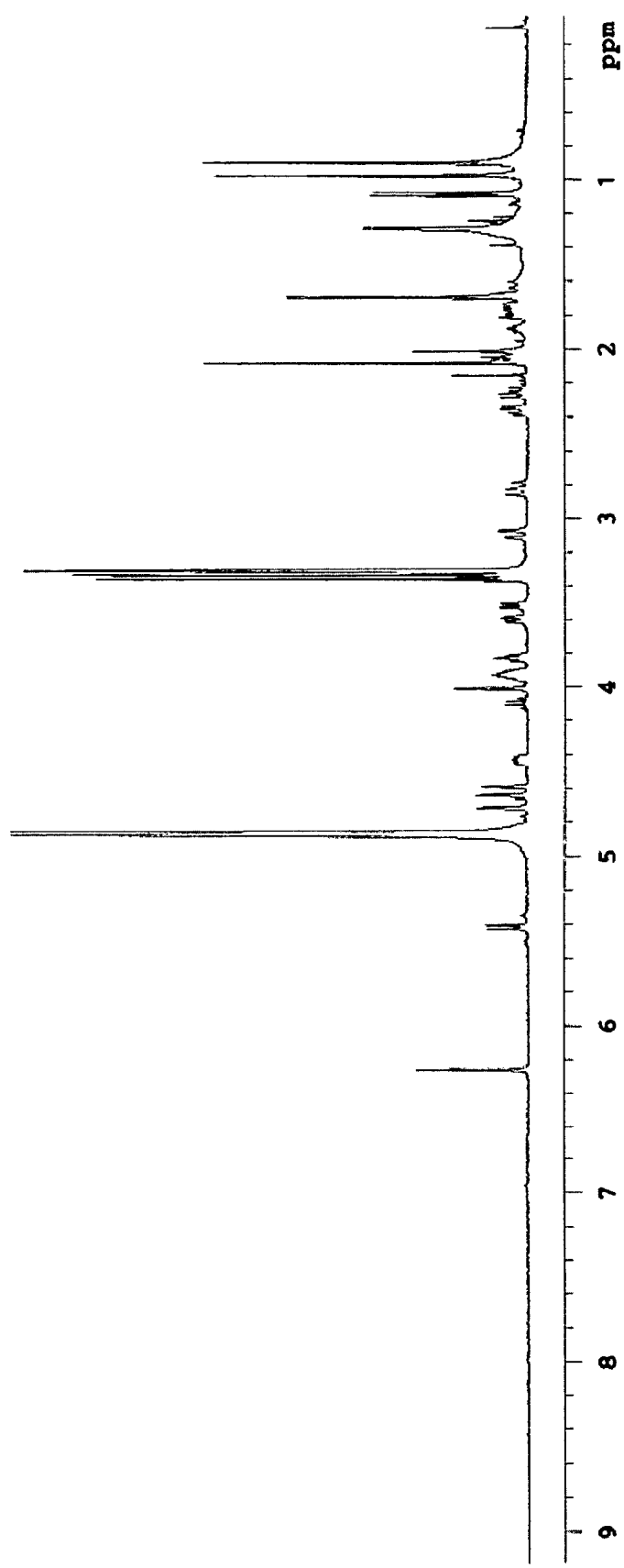
FIG. 6 is the $^1$H-NMR spectrum of compound 29-a in $CD_3OD$.

29-a: $^1$H NMR (CD$_3$OD; FIG. 6) δ 0.90 (s, 3H), 0.97 (s, 3H), 1.08 (d, 3H, J=7.2Hz), 1.64 (m, 1H), 1.70 (s, 3H), 1.78 (m, 2H), 1.88 (ddq, 1H, J=2.4, 6.4, 7.2 Hz), 2.04 (m, 1H), 2.09 (s, 3H), 2.25 (dd, 1H, J=8.0, 14.0 Hz), 2.37 (dd, 1H, J=6.0, 14.0 Hz), 2.83 (dd, 1H, J=12.0, 16.8 Hz), 3.09 (dd, 1H, J=3.2, 16.8 Hz), 3.34 (s, 3H), 3.36 (s, 3H), 3.51 (dd, 1H, J=1.6, 10.4 Hz), 3.60 (dd, 1H, J=4.4, 10.8 Hz), 3.83 (ddd, 1H, J=1.8, 6.0, 8.0 Hz), 3.93 (m, 2H), 4.01 (d, 1H, J=1.8 Hz), 4.44 (ddd, 1H, J=3.2, 6.4, 12.0 Hz), 4.64 (bs, 1H), 4.72 (bs, 1H), 5.41 (d, 1H, J=8.4 Hz), 6.26 (s, 1H); $^1$H NMR (CDCl$_3$) δ 0.92 (s, 3H), 1.00 (s, 3H), 1.09 (d, 3H, J=6.8 Hz), 1.55 (m, 1H), 1.74 (s, 3H), 1.78 (m, 1H), 1.86 (m, 2H), 2.03 (m, 1H), 2.07 (s, 3H), 2.35 (m, 2H), 2.80 (dd, 1H, J=12.0, 16.4 Hz), 2.94 (dd, 1H, J=3.6, 16.4 Hz), 3.38 (s, 3H), 3.39 (s, 3H), 3.53 (d, 1H, J=10.0 Hz), 3.68 (m, 1H), 3.85 (ddd, 1H, J=2.0, 7.6, 8.4 Hz), 3.92 (m, 2H), 4.09 (d, 1H, J=2.0 Hz), 4.25 (s, 1H), 4.53 (ddd, 1H, J=3.6, 5.2, 12.0 Hz), 4.71 (bs, 1H), 4.75 (bs, 1H), 5.40 (dd, 1H, J=8.0, 10.4 Hz), 6.30 (s, 1H), 7.14 (d, 1H, J=10.4 Hz), 11.21 (bs, 1H); MS (ES) m/z: 632.25 ([MNa]$^+$).

Figure 7:
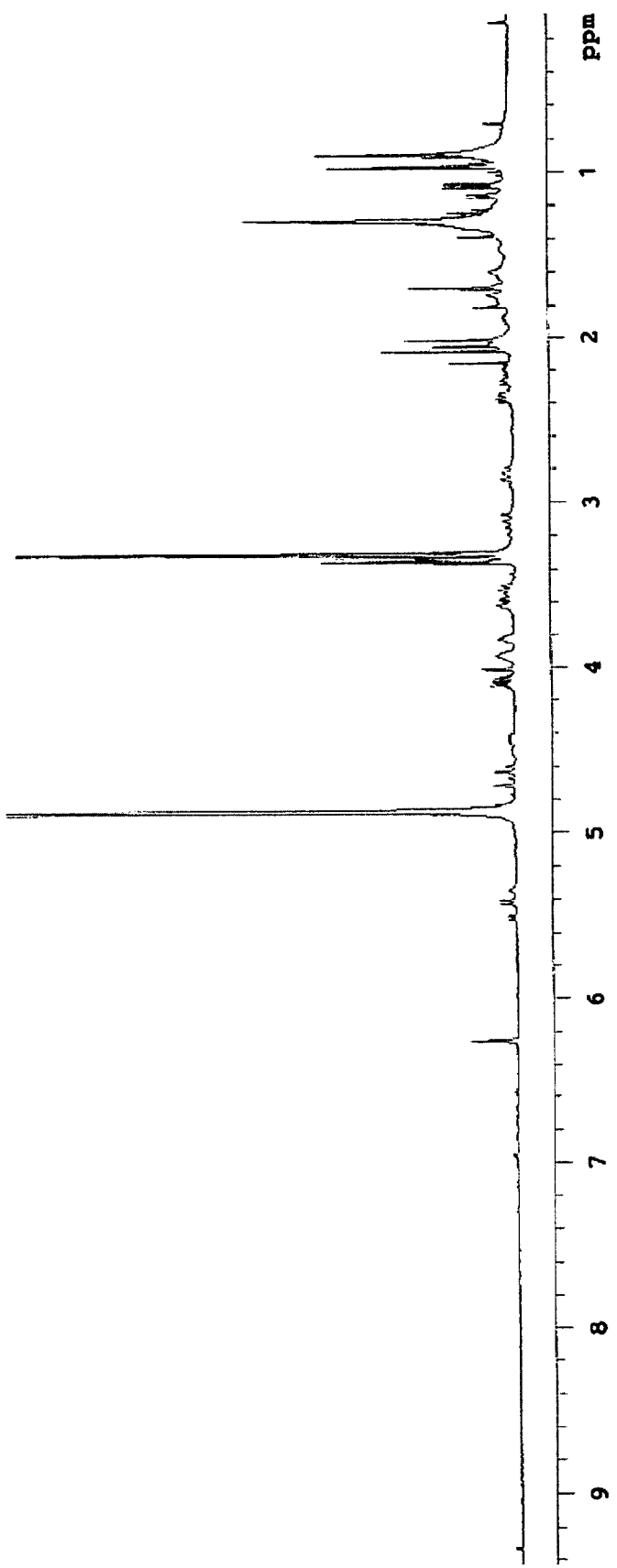
FIG. 7 is the $^1$H-NMR spectrum of a mixture of compounds 29-a and 29-b in $CD_3OD$.

29-b was obtained as a mixture with 29-a. The peaks that can be identified are: $^1$H NMR (CD$_3$OD; FIG. 7) δ 1.14 (d, 3H, J=6.8Hz), 1.64 (m, 1H), 1.81 (s, 3H), 3.17 (dd, 1H, J=2.8, 16.4 Hz), 3.36 (s, 3H), 3.37 (s, 3H), 4.49 (ddd, 1H, J=2.8, 6.4, 12.0 Hz), 4.60 (bs, 1H), 4.67 (bs, 1H), 5.50 (d, 1H, J=8.8 Hz), 6.26 (s, 1H); $^1$H NMR (CDCl$_3$) δ 0.92 (s, 3H), 0.98 (s, 3H), 1.15 (d, 3H, J=7.2 Hz), 1.79 (s, 3H), 2.07 (s, 3H), 3.05 (dd, 1H, J=3.0, 16.8 Hz), 3.37 (s, 3H), 3.41 (s, 3H), 4.80 (bs, 1H), 4.86 (bs, 1H), 5.35 (dd, 1H, J=6.8, 10.0 Hz), 6.30 (s, 1H), 7.16 (d, 1H, J=10.0 Hz), 11.23 (bs, 1H).

Biological Testing

The cytotoxicities of compounds 28-a, 28-b, and 29-a were evaluated against the human cancer cell lines HeLa, SK-MEL-5, and SK-MEL-28. The cytotoxicity evaluations were performed, over a concentration range of 0.2 nM to 20 μM, using the CellTiter-Glo™ Luminescent Cell Viability Assay, a product of Promega Corporation (Madison, Wis. USA), according to the protocol detailed in Promega's Technical Bulletin No. 288. Table 1 presents the results of these assays. Each value is the average value obtained from three experiments. GI$_{50}$ is the concentration that inhibits 50% growth; TGI is the concentration that inhibits 100% growth; and LC$_{50}$ is the concentration that kills 50% of the cells.

TABLE 1

Cytotoxicity of Compounds of the Invention

| Compound | | HeLa Concentration (nM) | SK-MEL-5 Concentration (nM) | SK-MEL-28 Concentration (nM) |
|---|---|---|---|---|
| 28-a | GI$_{50}$ | 0.23 | 0.3 | 0.23 |
| | TGI | 0.90 | 0.7 | 0.7 |
| | LC$_{50}$ | 1.6 | 1.3 | 1.2 |
| 29-a | GI$_{50}$ | 60 | 300 | 200 |
| | TGI | 200 | 800 | 550 |
| | LC$_{50}$ | 900 | 1700 | 1100 |
| 28-b | GI$_{50}$ | 80 | 300 | 110 |
| | TGI | 200 | 700 | 400 |
| | LC$_{50}$ | 900 | 1100 | 900 |

We claim:

1. A pharmaceutically acceptable salt or phosphate, ester, phosphate ester, or phosphonate ester of the compound of formula 28-a:

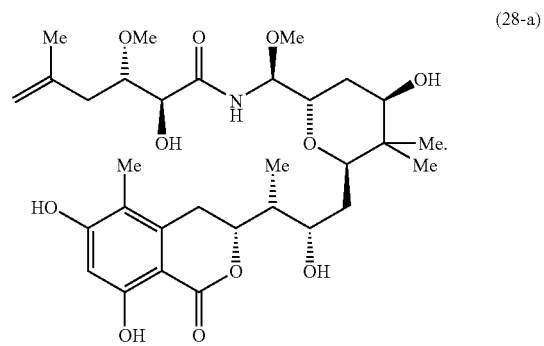

(28-a)

2. The pharmaceutically acceptable salt according to claim 1, wherein the salt is a lithium, sodium, or potassium salt.

3. A compound having one of the following formulae:

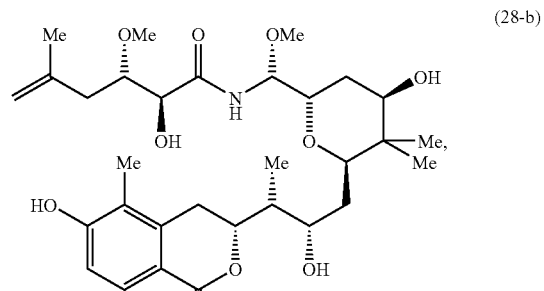

(28-b)

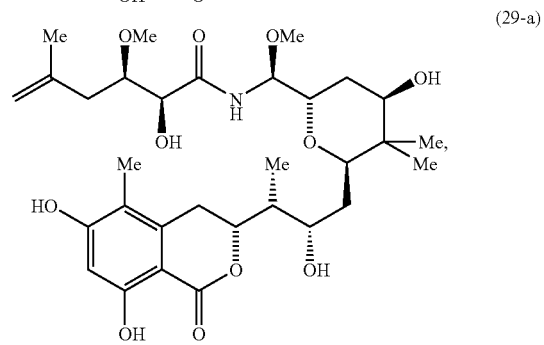

(29-a)

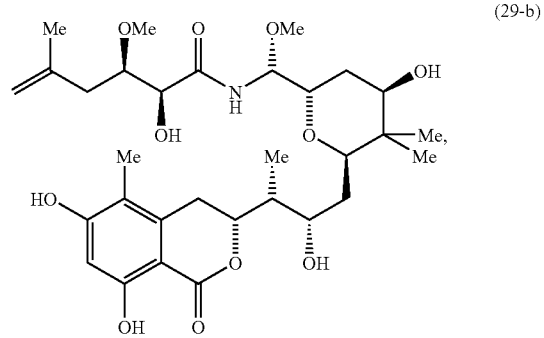

(29-b)

or a pharmaceutically acceptable salt thereof.

4. A pharmaceutical composition comprising the pharmaceutically acceptable salt according to claim 3 and a pharmaceutically acceptable carrier.

5. The pharmaceutical composition according to claim 4, wherein the pharmaceutically acceptable carrier comprises polyethylene glycol and saline solution.

6. The pharmaceutical composition according to claim 4, wherein the pharmaceutical composition is present as a lyophilized powder.

7. A pharmaceutical composition comprising the compound or a pharmaceutically acceptable salt thereof according to claim 1 and a pharmaceutically acceptable carrier.

8. The pharmaceutical composition according to claim 7, wherein the pharmaceutically acceptable carrier comprises polyethylene glycol and saline solution.

9. The pharmaceutical composition according to claim 7, wherein the pharmaceutical composition is present as a lyophilized powder.

10. A method for treating a subject suffering from a cancer that is selected from the group consisting of pancreatic cancer, breast cancer, lung cancer, colon cancer, prostate cancer, brain cancer, ovarian cancer, and cervical cancer, comprising administering to the subject a therapeutically effective amount of a compound having one of the following formulae, or a pharmaceutically acceptable salt, thereof:

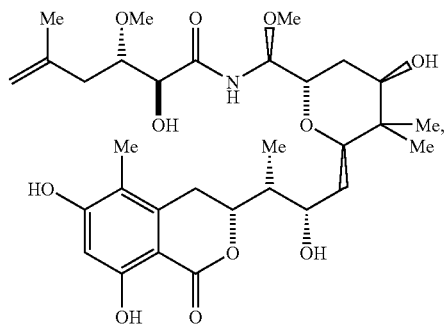

(28-a)

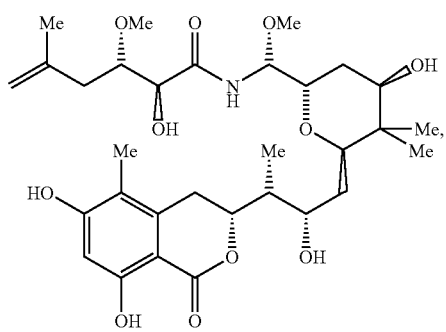

(28-b)

-continued

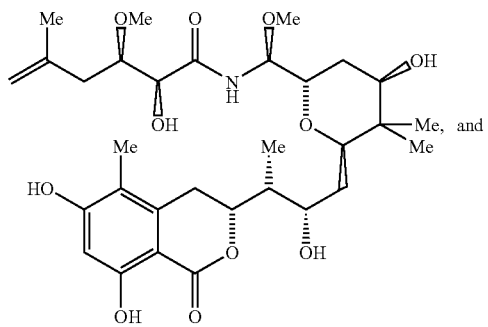

(29-a)

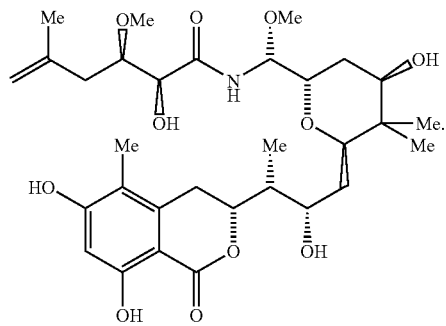

(29-b)

11. The method according to claim 10, wherein the compound has the formula 28-a:

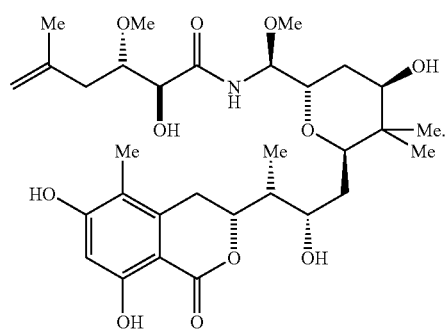

(28-a)

12. The method according to claim 10, wherein the compound is administered intravenously.

13. The method according to claim 10, wherein the dose of the compound is about 0.1 to about 30 mg/kg.

14. The method according to claim 13, wherein the dose of the compound is about 0.1 to about 2.0 mg/kg.

15. A process for preparing a compound having formula 28-a:

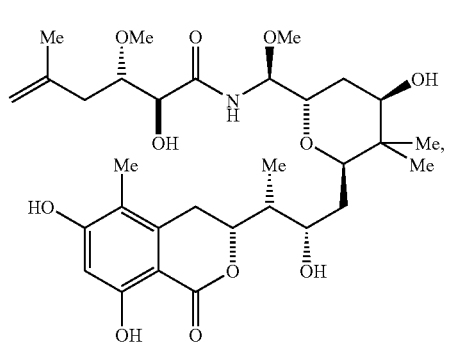

comprising the steps of reacting a compound of formula 25:

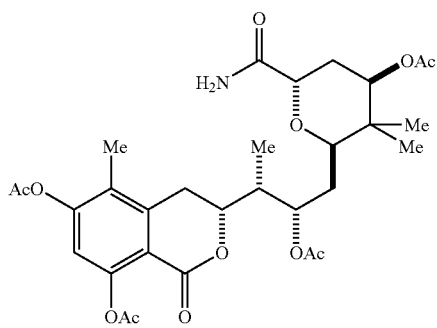

with a compound of formula anti-27:

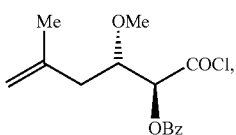

and deprotecting to give the compound having formula 28-a.

16. The process according to claim 15, further comprising the step of isolating the compound of formula 28-a.

17. An intermediate compound having the formula 20:

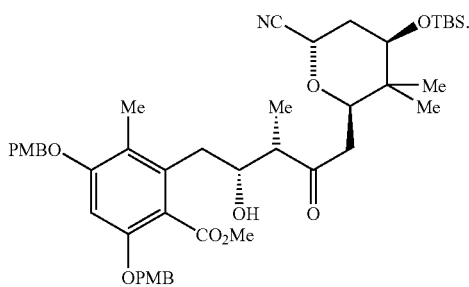

18. A process for preparing an intermediate compound having the formula 20:

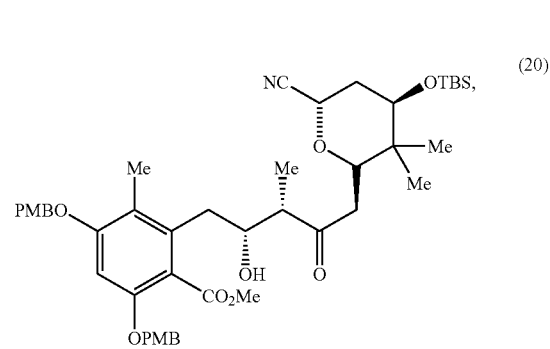

comprising the step of reacting a compound having the formula 6:

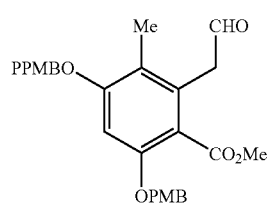

with a compound having the formula 7:

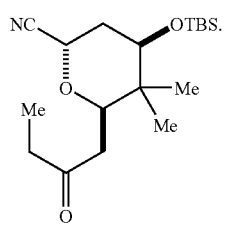

19. An intermediate compound having the formula 7:

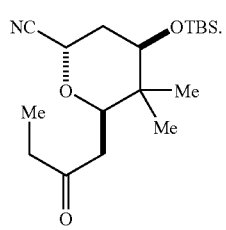

20. A process for preparing an intermediate compound having the formula 7:
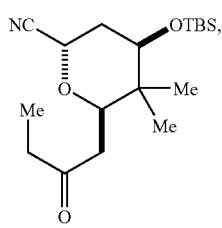
(7)
comprising the steps of
(a) ethylating a compound of formula 19:
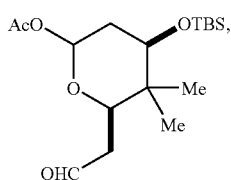
(19)
to give a compound of formula x:
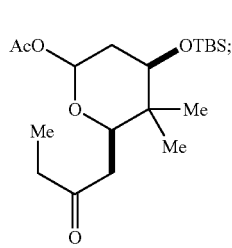
(x)
(b) reacting the compound of formula x with TMSCN to give and then isolating a compound of formula xi:
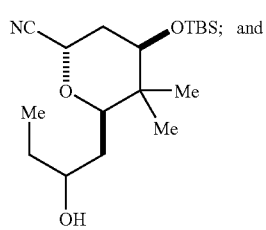
(xi)
(c) oxidizing the compound of formula xi to give the compound of formula 7.
* * * * *